United States Patent
Lang et al.

(10) Patent No.: US 7,763,643 B2
(45) Date of Patent: Jul. 27, 2010

(54) SUBSTITUTED THIOPHENES: COMPOSITIONS, PROCESSES OF MAKING, AND USES IN DISEASE TREATMENT AND DIAGNOSIS

(75) Inventors: Hans-Jochen Lang, Hofheim (DE); Uwe Heinelt, Wiesbaden (DE); Armin Hofmeister, Oppenheim (DE); Klaus Wirth, Kriftel (DE); Michael Gekle, Wurzburg (DE); Markus Bleich, Hunfelden-Dauborn (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/363,030

(22) Filed: Jan. 30, 2009

(65) Prior Publication Data

US 2009/0137630 A1 May 28, 2009

Related U.S. Application Data

(60) Continuation of application No. 11/863,608, filed on Sep. 28, 2007, now Pat. No. 7,488,746, which is a division of application No. 11/385,331, filed on Mar. 21, 2006, now Pat. No. 7,317,033, which is a continuation of application No. 10/448,851, filed on May 30, 2003, now Pat. No. 7,049,333.

(60) Provisional application No. 60/415,788, filed on Oct. 3, 2002.

(30) Foreign Application Priority Data

Jun. 4, 2002 (DE) ................................ 102 24 892

(51) Int. Cl.
*A61K 31/4178* (2006.01)
(52) U.S. Cl. .................. 514/388; 514/322; 514/395
(58) Field of Classification Search ............ 514/388, 514/395, 322
See application file for complete search history.

(56) References Cited

U.S. PATENT DOCUMENTS

| | | | |
|---|---|---|---|
| 3,758,476 | A | 9/1973 | Lindner et al. |
| 4,215,133 | A | 7/1980 | Stahle et al. |
| 4,882,342 | A | 11/1989 | Von Der Saal et al. |
| 4,927,834 | A | 5/1990 | Leinert et al. |
| 5,576,322 | A | 11/1996 | Takase et al. |
| 5,693,652 | A | 12/1997 | Takase et al. |
| 5,801,180 | A | 9/1998 | Takase et al. |
| 6,005,010 | A | 12/1999 | Schwark et al. |
| 6,060,607 | A | 5/2000 | Brands et al. |
| 6,737,423 | B2 | 5/2004 | Heinelt et al. |
| 7,317,033 | B2 * | 1/2008 | Lang et al. ............... 514/388 |
| 2003/0119754 | A1 | 6/2003 | Lackey et al. |
| 2004/0224965 | A1 | 11/2004 | Gericke et al. |
| 2004/0242627 | A1 | 12/2004 | Suzuki et al. |
| 2004/0254376 | A1 | 12/2004 | Suzuki et al. |
| 2005/0004197 | A1 | 1/2005 | Suzuki et al. |
| 2005/0004204 | A1 | 1/2005 | Suzuki et al. |

FOREIGN PATENT DOCUMENTS

| | | |
|---|---|---|
| DE | 19960204 | 6/2001 |
| EP | 0339814 | 11/1990 |
| EP | 0400835 | 12/1990 |
| EP | 0419210 | 3/1991 |
| EP | 0681006 | 11/1995 |
| EP | 0825178 | 6/2001 |
| WO | WO 82/02046 | 6/1982 |
| WO | WO 92/08693 | 5/1992 |
| WO | WO 96/14319 | 5/1996 |
| WO | WO 98/56376 | 12/1998 |
| WO | WO 99/24407 | 5/1999 |
| WO | WO 00/35860 | 6/2000 |
| WO | WO 01/21160 | 3/2001 |
| WO | WO 0121582 | 3/2001 |
| WO | WO 01/52847 | 7/2001 |
| WO | WO 0172742 | 10/2001 |
| WO | WO 0179186 | 10/2001 |
| WO | WO 02/30357 | 4/2002 |
| WO | WO 02/30358 | 4/2002 |
| WO | WO 02/053156 | 7/2002 |
| WO | WO 02/053158 | 7/2002 |
| WO | WO 02/053161 | 7/2002 |

(Continued)

OTHER PUBLICATIONS

Akhter, S., et. al., Squalamine, A Novel Cationic Steroid, Specifically Inhibits The Brush-Border Na+/H+ Exchanger Isoform NHE3, The American Physiological Society, 276, (Cell Physiology 45), (1999) pp. C136-C144.

(Continued)

*Primary Examiner*—Laura L. Stockton
(74) *Attorney, Agent, or Firm*—Jiang Lin

(57) ABSTRACT

The present invention comprises compounds and compositions comprising substituted thiophene derivatives with the following backbone structure:

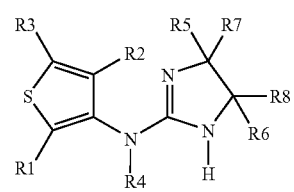

The compounds of this type are of useful in the treatment of various disorders, such as, respiratory disorders and snoring, acute and chronic disorders, disorders induced by ischemic and/or reperfusion events and by proliferative or fibrotic events, disorders of the central nervous system and lipid metabolism, diabetes, blood coagulation and infection by parasites.

5 Claims, No Drawings

FOREIGN PATENT DOCUMENTS

WO     WO 02/072538     9/2002

OTHER PUBLICATIONS

Dear, R.E.A., et. al., Reactiones Organicae, Synthesis, 1974, pp. 41-42.

Ernsberger, P., et. al., Clonidine Binds To Imidazole Binding Sites As Well As alpha2-Adrenoceptors In The Ventorolateral Medulla, European Journal Of Pharmacology, 134, 1, (1987) pp. 1-13.

Fliegel, L., et. al., Regulation And Characterization Of The Na+/H+ Exchanger, Biochem. Cell Biology, 76, (1998), pp. 735-741.

Golub, T.R., et. al., Molecular Classification of Cancer: Class Discovery and Class Prediction by Gene Expression Monitoring, Science; Oct. 15, 1999; vol. 286; pp. 531-537.

Jen, T., et. al., Amidines And Related Compounds. 6. Studies On Structure-Activity Relationships Of Antihypertensive And Antisecretory Agents Related To Clonidine, Journal of Medicinal Chemistry, 18, 1, (1975), pp. 90-99.

Ma, E., et. al., Expression And Localization Of Na+/H+ Exchangers In Rat Central Nervous System, Neuroscience, 79, 2, (1997), pp. 591-603.

Omar, A-Moshen, M.E. et. al., The Cyclodesulfurization Of Thio Compounds; XVI Dicyclohexylcarbodiimide As An Efficient Cyclodesulfurizing Agent In The Synthesis Of Heterocyclic Compounds From Various Thio Compounds, Synthesis, 1977, pp. 864-865.

Orlowski, J., et. al., Molecular Cloning Of Putative Members Of The Na/H Exchanger Gene Family, The Journal Of Biological Chemistry, 267, 13, (May 5, 1992), pp. 9331-9339.

Staab, H. A., et. al., Synthese Von Isothiocyanaten, Justus Liebigs Annalen Der Chemie, 657, (1962) pp. 104-107.

* cited by examiner

SUBSTITUTED THIOPHENES: COMPOSITIONS, PROCESSES OF MAKING, AND USES IN DISEASE TREATMENT AND DIAGNOSIS

This application is a Continuation of U.S. application Ser. No. 11/863,608, filed Sep. 28, 2007, which is a Divisional of U.S. application Ser. No. 11/385,331, filed Mar. 21, 2006, now issued as U.S. Pat. No. 7,317,033, which is a Continuation of U.S. application Ser. No. 10/448,851, filed May 30, 2003, now issued as U.S. Pat. No. 7,049,333, which claims the benefit of U.S. Provisional Application No. 60/415,788 filed Oct. 3, 2002.

FIELD OF THE INVENTION

The invention relates to the substituted thiophene compounds of formula I useful for treating and/or preventing various disorders. More particularly, the invention relates to the substituted thiophene compounds of formula I possessing potent inhibitory properties on the sodium/proton exchanger of subtype 3 ("NHE3"), which makes the compounds useful, in the form of a medicament, for the treatment of respiratory disorders and snoring, for the improving of the respiratory drive, for the treatment of acute and chronic disorders, disorders triggered by ischemic and/or reperfusion events and by proliferative or fibrotic events, and for the treatment or prophylaxis of disorders of the central nervous system and lipid metabolism, and diabetes, blood coagulation and infection by parasites.

BACKGROUND OF THE INVENTION

NHE3 is found in the body of various species, for example, in the gall bladder, the intestine and the kidney (Larry Fliegel et al., Biochem. Cell. Biol. 76: 735-741, 1998), but can also be detected in the brain (E. Ma et al., Neuroscience 79: 591-603).

The NHE3 inhibitors known to date are derived from compounds of the acylguanidine type (EP825178), of the nor-bornylamine type (DE199 60 204), of the 2-guanidino-quinazoline type (WO 0179186) or of the benzamidine type (WO0121582, WO0172742). Squalamine, which has also been described as NHE3 inhibitor (M. Donowitz et al. Am. J. Physiol. 276 (Cell Physiol. 45): C136-C144), is, according to current understanding, not, unlike the compounds of formula I, effective immediately, but rather via an indirect mechanism and thus reaches its maximum potency only after one hour. Such NHE3 inhibitors which act by a different mechanism are therefore suitable for use as combination partners for the present compounds according to the invention.

Clonidine, which is similar to the compounds described here, is known as a weak NHE inhibitor. However, its action on the NHE3 of the rat is, with a half-maximal inhibitory concentration ($IC_{50}$) of 620 µM, extremely moderate. In contrast, it shows a certain selectivity for the NHE2 (J. Orlowski et al. J. Biol. Chem. 268, 25536). It would therefore be more accurate to refer to clonidine as an NHE2 inhibitor. In addition to the weak NHE action, clonidine has a high affinity for the adrenergic alpha2 receptor and the imidazoline I1 receptor, mediating a strong hypotensive action (Ernsberger et al., Eur. J. Pharmacol. 134, 1, 1987).

Clonidine-like compounds having a thiophene ring instead of the phenyl ring are known from DE1941761. These known compounds differ from the structures of formula I described in the present invention in that they have considerably smaller radicals R7 and R8 and in particular by the fact that R7 and R8 are not capable of forming a joint ring.

By these differences in the substituents R7 and R8, it is possible to eliminate the undesirable clonidine-like cardiovascular effects described above, which are mediated by the alpha-adrenoceptor action. At the same time, owing to these differences in the substituents, the NHE-inhibiting properties of the compounds described herein are enhanced to the micromolar and submicromolar range, whereas the compounds known from DE1941761 show only extremely weak NHE-inhibiting effects, if any.

The present invention provides a different kind of NHE3 inhibitors.

SUMMARY OF THE INVENTION

A primary object of the present invention is to provide compounds of formula I

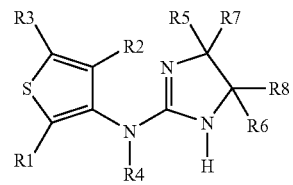

in which:

R1 and R2
  independently of one another are H, F, Cl, Br, I, CN, $NO_2$, $-(X)_n-C_qH_{2q}-Z$, cycloalkyl having 3, 4, 5 or 6 carbon atoms, alkenyl having 2, 3 or 4 carbon atoms, alkenylalkyl having 3 or 4 carbon atoms, ethynyl or alkylalkynyl having 3 or 4 carbon atoms;

n is zero or 1;

X is oxygen, NH, N—$CH_3$, $S(O)_k$;
  k is zero, 1 or 2;
  q is zero, 1, 2, 3, 4, 5 or 6;
  Z is hydrogen or $C_mF_{2m+1}$;
  m is zero, 1, 2, 3 or 4;

R3 is hydrogen, methyl, F, Cl, Br, I, CN, $S(O)_k$—$CH_3$, —$NO_2$, —O—$CH_3$;
  k is zero, 1 or 2;

R4 is hydrogen, cycloalkyl having 3, 4, 5, or 6 carbon atoms, alkenyl having 2, 3 or 4 carbon atoms, alkenylalkyl having 3 or 4 carbon atoms, ethynyl or alkylalkynyl having 3 or 4 carbon atoms, —$C_rH_{2r}$—Y;
  r is zero, 1, 2, 3 or 4;
  Y is hydrogen or trifluoromethyl;

R5 and R6 are hydrogen or together are a bond;

R7 and R8
  independently of one another are ($C_3$-$C_5$)-alkyl, ($C_2$-$C_5$)-alkenyl, ($C_2$-$C_5$)-alkynyl, ($C_3$-$C_6$)-cycloalkyl or ($C_4$-$C_6$)-cycloalkenyl or R7 and R8
  together are an alkylene chain comprising 3 to 8 carbon atoms;
  where none, some or all of their hydrogen atoms may be replaced by fluorine atoms;

or

R7 and R8
  together are a radical

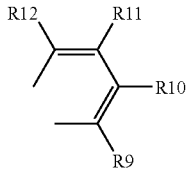

where R5 and R6 together form a bond;
  R10 and R11 independently of one another are hydrogen, fluorine, chlorine, bromine, methyl, CN, OH, —O—$CH_3$, $NO_2$, $NH_2$ or —$CF_3$;

R9 and R12
  are hydrogen or F;
or
one of the substituents R9 and R12
  is hydrogen;
  and the other is F, Cl, Br, I, CN, $NO_2$, COOH, CO—NR13R14, $SO_2$—NR13R14, alkenyl having 2, 3 or 4 carbon atoms, alkenylalkyl having 3 or 4 carbon atoms, ethynyl, alkylalkynyl having 3 or 4 carbon atoms or —$(X)_n$—$C_qH_{2q}$—Z;
  R13 and R14
    are identical or different hydrogen or alkyl having 1, 2, 3 or 4 carbon atoms;
  or
  R13 and R14 together with the nitrogen to which they are attached form a saturated 5-, 6- or 7-membered ring;
  n is zero or 1;
  X is oxygen, NH, N—$CH_3$, $S(O)_k$;
    k is zero, 1 or 2;
  q is zero, 1, 2, 3, 4, 5 or 6;
  and
  Z is hydrogen or $C_mF_{2m+1}$;
    m is zero, 1, 2, 3 or 4;

and their pharmaceutically acceptable salts, and their trifluoroacetic acid salts.

One embodiment relates to compounds of formula I in which
R1 and R2
  independently of one another are H, F, Cl, Br, I, CN, $NO_2$, —$(X)_n$—$C_qH_{2q}$—Z, cycloalkyl having 3, 4, 5 or 6 carbon atoms, alkenyl having 2, 3 or 4 carbon atoms, alkenylalkyl having 3 or 4 carbon atoms, ethynyl or alkylalkynyl having 3 or 4 carbon atoms;
  n is zero or 1;
  X is oxygen, NH, N—$CH_3$, $S(O)_k$;
    k is zero, 1 or 2;
  q is zero, 1, 2, 3, 4, 5 or 6;
  Z is hydrogen or $C_mF_{2m+1}$;
    m is zero, 1, 2, 3 or 4;
R3 is hydrogen, methyl, F, Cl, Br, I, CN, $S(O)_k$—$CH_3$, —$NO_2$, —O—$CH_3$;
R4 is hydrogen, cycloalkyl having 3, 4, 5, or 6 carbon atoms, alkenyl having 2, 3 or 4 carbon atoms, alkenylalkyl having 3 or 4 carbon atoms, ethynyl or alkylalkynyl having 3 or 4 carbon atoms, —$C_qH_{2q}$—Z;
  q is zero, 1, 2, 3 or 4;
  Z is hydrogen or trifluoromethyl;
R5 and R6
  are hydrogen or together are a bond;
R7 and R8
  independently of one another are ($C_3$-$C_5$)-alkyl, ($C_2$-$C_5$)-alkenyl, ($C_2$-$C_5$)-alkynyl, ($C_3$-$C_6$)-cycloalkyl or ($C_4$-$C_6$)-cycloalkenyl
or
R7 and R8
  together are an alkylene chain comprising 3 to 8 carbon atoms;
  where none, some or all of their hydrogen atoms may be replaced by fluorine atoms;
or
R7 and R8
  together are a radical

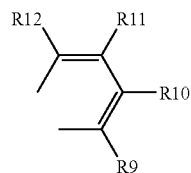

where R5 and R6 together form a bond;
R9, R10 and R11
  independently of one another are hydrogen, fluorine, chlorine, bromine, methyl, CN, OH, —O—$CH_3$, $NO_2$, $NH_2$ or —$CF_3$;
R9 and R12
  are hydrogen;
or
one of the substituents R9 and R12
  is hydrogen;
  and the other is F, Cl, Br, I, CN, $NO_2$, COOH, CO—NR13R14, $SO_2$—NR13R14, alkenyl having 2, 3 or 4 carbon atoms, alkenylalkyl having 3 or 4 carbon atoms, ethynyl, alkylalkynyl having 3 or 4 carbon atoms or —$(X)_n$—$C_qH_{2q}$—Z;
  R13 and R14
    are identical or different hydrogen or alkyl having 1, 2, 3 or 4 carbon atoms;
  n is zero or 1;
  X is oxygen, NH, N—$CH_3$, $S(O)_k$;
    k is zero, 1 or 2;
  q is zero, 1, 2, 3, 4, 5 or 6;
  and
  Z is hydrogen or $C_mF_{2m+1}$;
    m is zero, 1, 2, 3 or 4;

and their pharmaceutically acceptable salts, and their trifluoroacetic acid salts.

Preference is given to compounds of formula I, in which:
R1 and R2
  independently of one another are H, F, Cl, Br, $CH_3$, $CF_3$, $SO_2CH_3$, $SO_2NH_2$;
  but where at most one of the substituents R1 and R2 is hydrogen;
R3 is hydrogen, F or Cl;
R4 is hydrogen, alkyl having 1, 2, 3 or 4 carbon atoms, or cyclopropyl;
R5 and R6
  are hydrogen or together are a bond;
R7 and R8
  together are an alkylene chain comprising 3, 4, 5, 6, 7 or 8 carbon atoms;
or
R7 and R8
  together are a radical

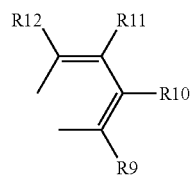

where R5 and R6 together form a bond;
R10 and R11
  independently of one another are hydrogen, OH, fluorine or chlorine;

R9 and R12
  are hydrogen;
or
one of the substituents R9 and R12
  is hydrogen;
  and the other is F, Cl, Br, CN, COOH, CO—NR13R14, SO$_2$—NR13R14 or —(X)$_n$—C$_q$H$_{2q}$—Z;
R13 and R14
  are identical or different hydrogen or methyl;
n is zero or 1;
X is oxygen, NH, N—CH$_3$ or S(O)$_k$;
  k is zero, 1 or 2;
q is zero, 1, 2, 3 or 4;
Z is hydrogen or CF$_3$;
and their pharmaceutically acceptable salts, and their trifluoroacetic acid salts.

Particular preference is given to compounds of formula I in which:
R1 and R2
  independently of one another are F, Cl, Br, CH$_3$ or CF$_3$;
R3 is hydrogen;
R4 is hydrogen, methyl, ethyl;
R5 and R6
  are hydrogen or together are a bond;
R7 and R8
  together are an alkylene chain comprising 3, 4, 5, 6, 7 or 8 carbon atoms;
or
R7 and R8
  together are a radical

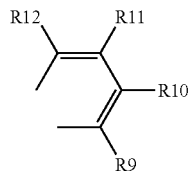

where R5 and R6 together form a bond;
R10 and R11
  independently of one another are hydrogen, OH or fluorine;
R9 and R12
  are hydrogen;
or
one of the substituents R9 and R12
  is hydrogen;
  and the other is F, Cl, Br or —(X)$_n$—C$_q$H$_{2q}$—Z;
n is zero or 1;
X is oxygen, NH, N—CH$_3$ or S(O)$_k$;
  k is zero, 1 or 2;
q is zero or 1;
z is hydrogen or CF$_3$;
and their pharmaceutically acceptable salts, and their trifluoroacetic acid salts.

Very particular preference is given to the following compounds of formula I, selected from the group consisting of:
trans-R,R-2-chloro-3N-(3a,4,5,6,7,7a-hexahydro-1H-2-benzimidazolyl)-4-methyl-3-thienylamine,
trans-RR-2-bromo-3N-(3a,4,5,6,7,7a-hexahydro-1H-2-benzimidazolyl)-4-methyl-3-thienylamine,
2-chloro-3N-(2-benzimidazolyl)-4-methyl-3-thienylamine,
2-bromo-3N-(2-benzimidazolyl)-4-methyl-3-thienylamine,
2-chloro-3N-(4-methyl-2-benzimidazolyl)-4-methyl-3-thienylamine,
2-chloro-3N-(5-fluoro-2-benzimidazolyl)-4-methyl-3-thienylamine,
2-chloro-3N-(4-chloro-2-benzimidazolylamino)-4-methylthiophene,
2-bromo-3N-(4-chloro-2-benzimidazolylamino)-4-methylthiophene,
2-bromo-3N-(4-fluoro-2-benzimidazolylamino)-4-methylthiophene,
2-chloro-3N-(4-fluoro-2-benzimidazolylamino)-4-methylthiophene,
2-chloro-3N-(4-hydroxy-2-benzimidazolylamino)-4-methylthiophene,
(1H-benzimidazol-2-yl)-(2-chloro-4-methylthiophen-3-yl)-methylamine,
(2-bromo-4-methylthiophen-3-yl)-(5-fluoro-1H-benzimidazol-2-yl)-amine,
2,4-dichloro-3N-(2-benzimidazolylamino)thiophen,
2-bromo-4-chloro-3N-(2-benzimidazolylamino)thiophen,
2,4-dichloro-3N-(4-methyl-2-benzimidazolyl-amino)thiophen, trans-R,R-2,4-Dichlor-3N-(3a,4,5,6,7,7a-hexahydro-1H-2-benzimidazolyl)-3-thienylamin,
2,4-dichloro-3N-(4-chlor-2-benzimidazolyl-amino)thiophen
and
2-chloro-3N-(2-benzimidazolylamino)-4-methylthiophene and their pharmaceutically acceptable salts, for example the hydrochloride or the hydrobromide or the methanesulfonate of each of the compounds.

The compounds of formula I can be present in the form of their salts. Suitable acid addition salts are salts of all pharmacologically acceptable acids, for example halides, in particular hydrochlorides, hydrobromides, lactates, sulfates, citrates, tartrates, acetates, phosphates, methylsulfonates, benzenesulfonates, p-toluenesulfonates, adipinates, fumarates, gluconates, glutamates, glycerolphosphates, maleates, benzoates, oxalates and pamoates. This group also corresponds to the physiologically acceptable anions; but also trifluoroacetates.

If the compounds contain an acid group, they are capable of forming salts with bases, for example as alkali metal salts, preferably sodium or potassium salts, or as ammonium salts, for example as salts with ammonia or organic amines or amino acids. They can also be present as zwitterion.

If the compounds of formula I contain one or more centers of asymmetry, the compounds can independently be both S- and R-configured. The compounds can be present as optical isomers, as diastereomers, as racemates or as mixtures thereof.

The compounds of formula I can furthermore be present as tautomers or as a mixture of tautomeric structures. This refers, for example, to the following tautomers:

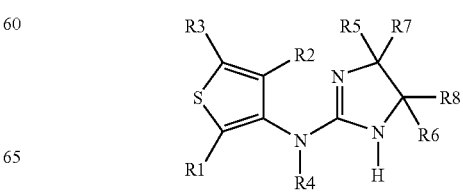

-continued

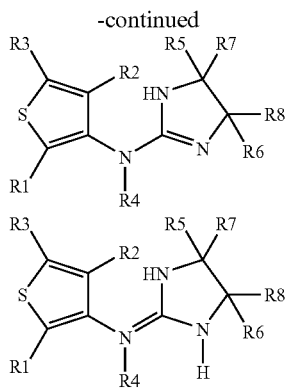

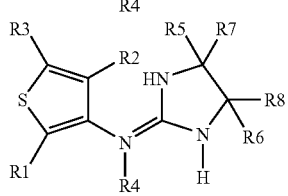

(if R4 = H)

Alkyl radicals can be straight-chain or branched. This also applies when they carry substituents or are present as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methyl-propyl), tert-butyl (=1,1-dimethylethyl), n-pentyl, isopentyl, tert-pentyl, neo-pentyl or hexyl. Preferred alkyl radicals are methyl, ethyl, n-propyl, isopropyl, n-butyl, tert-butyl, n-pentyl, n-hexyl. In alkyl radicals, one or more, for example 1, 2, 3, 4, 5, 6, 7, 8 or 9, hydrogen atoms may be substituted by fluorine atoms. Examples of such fluoroalkyl radicals are trifluoromethyl, 2,2,2-trifluoroethyl, pentafluoroethyl, heptafluoroisopropyl. Substituted alkyl radicals may be substituted in any positions.

Alkenyl radicals may be straight-chain or branched. This also applies when they are present as substituents, for example in alkenylalkylene. The alkenyl radicals can be unsaturated in different positions. Examples of alkenyl radicals are ethenyl, propenyl or butenyl.

Alkynyl radicals can be straight-chain or branched. This also applies when they are present as substituents, for example in alkynylalkylene. The alkynyl radicals can be unsaturated in different positions. Examples of alkynyl radicals are ethynyl, propynyl or butynyl.

Examples of cycloalkyl radicals are cyclopropyl, cyclobutyl, cyclopentyl or cyclohexyl. Substituted cycloalkyl radicals can be substituted in any positions. The cycloalkyl radicals may also be present branched as alkylcycloalkyl or cycloalkylalkyl.

Also described are methods for preparing compounds according to the invention. Thus, the substances described by formula I can be prepared in a manner known to the person skilled in the art from the isothiocyanate II parent compounds and the appropriate diamines III.

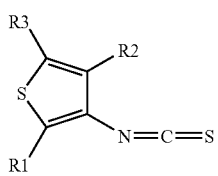

II

-continued

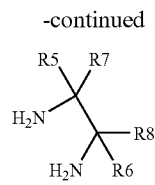

III

The thiourea derivative which is formed as an intermediate is cyclized using methyliodide (Synthesis, 1974, 41-42) or carbodiimide (Synthesis, 1977, 864-865) or using p-toluenesulfonyl chloride to give the corresponding compound of formula I. If the isothiocyanates II employed here are not commercially available, they can be prepared in a manner known from the literature from the corresponding aminothiophene derivatives, using methods known to the person skilled in the art, for example by treatment with thiophosgene (J. Med. Chem., 1975, 18, 90-99) or thiocarbonyl diimidazole (Justus Liebigs Ann. Chem., 1962, 657, 104).

In addition to the isothiocyanates II described above, it is also possible to successfully react the isocyanates IV

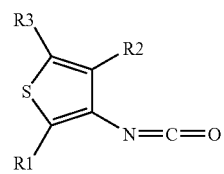

IV with amines of the type of formula III to give the compounds of formula I. Here, the urea derivative which is formed as an intermediate is cyclized using phosphorus oxychloride to give the corresponding compounds of formula I.

In the present invention, it was surprisingly possible to demonstrate that the compounds described are potent inhibitors of the sodium/proton exchanger (NHE), in particular the sodium/proton exchanger of subtype 3 (NHE3).

Owing to the NHE-inhibitory properties, the compounds of formula I are suitable for the prevention and treatment of diseases caused by an activation of NHE or by an activated NHE, and of diseases which are sequelae of damage caused by NHE.

Since NHE inhibitors act predominantly via influencing cellular pH regulation, they can be combined in a favorable manner with other compounds which also regulate the intracellular pH, suitable combination partners being inhibitors of the enzyme group of the carbonate dehydratases, inhibitors of the bicarbonate-ion-transporting systems, such as the sodium bicarbonate cotransporter (NBC) or the sodium-dependent chloride/bicarbonate exchanger (NCBE), and also NHE inhibitors having inhibitory action on other NHE subtypes, since they can modulate or enhance the pharmacologically relevant pH-regulating effects of the NHE inhibitors described herein.

The use of the compounds according to the invention relates to the prevention and treatment of acute and chronic diseases in veterinary and human medicine.

The pharmacological action of the compounds of formula I is characterized in that they induce an improvement in the respiratory drive and can therefore be used in the treatment of disturbed respiratory conditions for example in the following clinical conditions and diseases: disturbed central respiratory drive (e.g. central sleep apnea, sudden infant death, postoperative hypoxia), muscular-related respiratory disorders, respiratory disorders after long-term ventilation, respiratory disorders during adaptation in a high mountain area, obstructive and mixed forms of sleep apnea, acute and chronic lung diseases with hypoxia and hypercapnia.

The compounds additionally increase the muscle tone of the upper airways, so that snoring is suppressed. As a result, the compounds mentioned are advantageously used for preparing a medicament for the prevention and treatment of sleep apnea and muscular-related respiratory disturbances and for preparing a medicament for the prevention and treatment of snoring.

A combination of an NHE inhibitor of formula I with a carboanhydrase inhibitor (e.g. acetazolamide) can be advantageous, the latter producing metabolic acidosis and thereby already increasing respiratory activity, may prove to be advantageous as a result of increased action and decreased use of active compound.

Owing to their NHE3-inhibitory action, the compounds according to the invention spare cellular energy resources which, during toxic and pathogenic events, are rapidly depleted, thus resulting in cell damage or cell death. Here, the high-energy ATP-consuming resorption of sodium in the proximal tubulus is, under the influence of the compounds of formula I, temporarily switched off, and the cell is thus able to survive an acute pathogenic, ischemic or toxic situation. The compounds are therefore suitable by way of example for use as drugs for treating ischemic noxa, for example acute kidney failure.

Furthermore, the compounds are also suitable for treating all chronic renal disorders and forms of nephritis which, as a consequence of increased elimination of protein, result in chronic kidney failure. Accordingly, the compounds of formula I are suitable for preparing a medicament for the treatment of diabetic late damage, diabetic nephropathy and chronic renal disorders, in particular all inflammations of the kidney (nephritides) associated with increased elimination of protein/albumin.

It has been shown that the compounds used according to the invention have mild laxative action and, accordingly, can also be used advantageously as laxatives or for the prophylaxis of intestinal obstruction.

Furthermore, the compounds according to the invention can be used advantageously for the prevention and therapy of acute and chronic disorders of the intestinal tract triggered, for example, by ischemic states in the intestinal region and/or by subsequent reperfusion or by states and events of inflammation. Such complications can occur, for example, by lack of intestinal peristalsis, as is frequently observed, for example, after surgical interventions, in the case of bowel obstruction or in cases of strongly reduced intestinal motility.

Using the compounds according to the invention, it is possible to prevent gallstone formation.

The NHE inhibitors according to the invention are generally suitable for treating diseases caused by ischemia and by reperfusion.

As a result of their pharmacological properties, the compounds according to the invention are suitable for use as antiarrhythmics.

Owing to their cardioprotective component, the NHE inhibitors of formula I are highly suitable for infarct prophylaxis and infarct treatment and for treatment of angina pectoris, and they also inhibit, or strongly reduce, in a preventative manner, the pathophysiological processes which contribute to ischemically induced damage, in particular those which trigger ischemically induced cardiac arrhythmias. Owing to their protective action against pathological hypoxic and ischemic situations, the compounds of formula I used according to the invention can, as inhibitors of the cellular $Na^+/H^+$ exchange mechanism, be used as medicaments for treating all acute or chronic damage caused by ischemia, or diseases induced primarily or secondarily by this damage.

This relates to their use as medicaments for surgical interventions. Thus, the compounds according to the invention can be used for organ transplantations, where the compounds can be used both for protecting the organs in the donor before and during removal, for protecting organs that have been removed, for example during treatment with or storage in physiological bath fluids, and also during transfer into the recipient organism pretreated with compounds of formula I.

The compounds are also useful medicaments with protective action during angioplastic surgical interventions, for example on the heart, but also in peripheral organs and vessels.

Since NHE inhibitors protect human tissue and organs not only effectively against damage caused by ischemia and reperfusion but also against the cytotoxic action of medicaments used in particular in cancer therapy and the therapy of autoimmune diseases, the combined administration with compounds of formula I is suitable for suppressing or reducing the cytotoxic effects of a therapy. By reducing the cytotoxic effects, in particular cardiotoxicity, by comedication with NHE inhibitors it is furthermore possible to increase the dose of the cytotoxic therapeutics and/or to prolong medication with such medicaments. The therapeutic benefit of such a cytotoxic therapy can be enhanced considerably by combination with NHE inhibitors.

The compounds of formula I are suitable in particular for improving the therapy with medicaments having an undesirable cardiotoxic component.

Owing to their protective action against ischemically induced damage, the compounds according to the invention are also suitable for use as medicaments for treating ischemias of the nervous system, in particular the central nervous system, where they can be used, for example, for treating stroke or cerebral edema.

The compounds of formula I are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. Here, the NHE inhibitors according to the invention can be used on their own or in combination with other substances having antiepileptic action or with antipsychotic active compounds, or carbonate dehydratase inhibitors, for example acetazolamide, and also with other inhibitors of NHE or of the sodium-dependent chloride/bicarbonate exchanger (NCBE).

In addition, the compounds of formula I according to the invention are also suitable for treating types of shock, such as, for example, of allergic, cardiogenic, hypovolemic and bacterial shock.

The compounds of formula I can also be used for the prevention and treatment of thrombotic disorders since, as NHE inhibitors, they are also capable of inhibiting platelet aggregation themselves. In addition, they can prevent or inhibit excessive release of mediators of inflammation and coagulation, in particular of the von Willebrand factor and thrombogenic selecting proteins which takes place following ischemia and reperfusion. It is thus possible to reduce and eliminate the pathogenic effect of significant thrombogenic factors. Accordingly, the NHE inhibitors of the present invention can be combined with other compounds having anticoagulative and/or thrombolytic action, such as, for example, recombinant or natural tissue plasminogen activator, streptokinase, urokinase, acetylsalicylic acid, thrombin antagonists, factor Xa antagonists, medicaments with fibrinolytic action, thromboxane receptor antagonists, phosphodiesterase inhibitors, factor VIIa antagonists, clopidogrel, ticlopidine, etc. Combined use of the present NHE inhibitors with NCBE inhibitors and/or with inhibitors of carbonate dehydratase, such as, for example, with acetazolamide, is particularly beneficial.

Furthermore, the compounds of formula I according to the invention have strong inhibiting action on cell proliferation, for example on fibroblast cell proliferation and proliferation of smooth vascular muscle cells. The compounds of formula I are therefore useful therapeutics for diseases in which cell proliferation is a primary or secondary cause and can therefore be used as antiatherosclerotics, as agents against chronic kidney failure and against neoplastic diseases. Thus, they can be used for treating organ hypertrophy and hyperplasia, for example of the heart and the prostate. Compounds of formula I are therefore suitable for the prevention and treatment of cardiac insufficiency (congestive heart failure=CHF) and for the treatment and prevention of prostate hyperplasia and prostate hypertrophy.

The compounds of formula I furthermore delay or prevent fibrotic disorders. Thus, they are excellent agents for treating fibroses of the heart, and also pulmonary fibrosis, liver fibrosis, kidney fibrosis and other fibrotic disorders.

Since there is significant elevation of NHE in essential hypertensives, the compounds of formula I are suitable for the prevention and treatment of high blood pressure and of cardiovascular disorders.

Here, they can be used for the treatment of high blood pressure and of cardiovascular disorders on their own or with a suitable combination and formulation cocomponent. Thus, it is possible, for example, to combine one or more diuretics having thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone, with compounds of formula I. Furthermore, the NHE inhibitors of the present invention can be used in combination with calcium antagonists such as verapamil, diltiazem, amlodipine or nifedipine, and also with ACE inhibitors, such as, for example, ramipril, enalapril, lisinopril, fosinopril or captopril. Further favorable combination partners include beta-blockers such as metoprolol, albuterol etc., antagonists of the angiotensin receptor and its receptor subtypes, such as losartan, irbesartan, valsartan, omapatrilat, gemopatrilat, endothelin antagonists, renin inhibitors, adenosine receptor agonists, inhibitors and activators of calcium channels, such as glibenclamide, glimepiride, diazoxide, cromakalim, minoxidil and its derivatives, activators of the mitochondrial ATP-sensitive potassium channel (mitoK (ATP) channel), inhibitors of other potassium channels, such as inhibitors of Kv1.5 etc.

Owing to their antiphlogistic action, the NHE inhibitors can be used as antiinflammatory agents. Mechanistically interesting is the inhibition of the release of mediators of inflammation. Thus, the compounds can be used alone or in combination with an antiphlogistic agent for the prevention or treatment of chronic and acute inflammatory disorders. The combination partners used are advantageously steroidal and non-steroidal antiinflammatory agents.

Moreover, it has been found that compounds of formula I exert a beneficial influence on serum lipoproteins. They can therefore be used for the prophylaxis and regression of atherosclerotic changes by excluding a causal risk factor. This includes not only primary hyperlipidemias but also certain secondary hyperlipidemias as are encountered, for example, in diabetes. Additionally, the compounds of formula I reduce infarcts induced by metabolic anomalies considerably and, in particular, lead to a significant reduction in the size and severity of the infarct induced.

Accordingly, the compounds mentioned are used advantageously for preparing a medicament for the treatment of hypercholesterolemia, for preparing a medicament for the prevention of atherogenesis, for preparing a medicament for the prevention and treatment of atherosclerosis, for preparing a medicament for the prevention and treatment of diseases induced by elevated cholesterol levels, for preparing a medicament for the prevention and treatment of diseases induced by endothelial dysfunction, for preparing a medicament for the prevention and treatment of hypertension induced by atherosclerosis, for preparing a medicament for the prevention and treatment of thromboses induced by atherosclerosis, for preparing a medicament for the prevention and treatment of ischemic damage and post-ischemic reperfusion damage induced by hypercholesterolemia and endothelial dysfunction, for preparing a medicament for the prevention and treatment of cardiac hypertrophies and cardiomyopathies and congestive heart failure (CHF), for preparing a medicament for the prevention and treatment of coronary vasospasms and myocardial infarcts induced by hypercholesterolemia and endothelial dysfunction, for preparing a medicament for the treatment of the conditions mentioned in combination with hypotensive substances, preferably with angiotensin converting enzyme (ACE) inhibitors and angiotensin receptor antagonists. A combination of an NHE inhibitor of formula I with an active compound that lowers the lipid concentration in the blood, preferably an HMG-CoA reductase inhibitor (for example lovastatin or pravastatin), the latter having hypolipidemic action, thereby enhancing the hypolipidemic properties of the NHE inhibitor of formula I, has been found to be a favorable combination with increased action and reduced use of active compound.

Thus, compounds of formula I bring about effective protection against endothelial damage of various origins. Owing to this protection of the vessels against the syndrome of endothelial dysfunction, compounds of formula I are useful medicaments for the prevention and treatment of coronary vasospasms, peripheral vascular diseases, in particular intermittent claudication, of atherogenesis and atherosclerosis, of left-ventricular hypertrophy and of dilated cardiomyopathy, and of thrombotic disorders.

Moreover, NHE inhibitors of formula I are suitable for treating non-insulin-dependent diabetes (NIDDM) where for example insulin resistance is suppressed. Here, to enhance antidiabetic efficacy and quality of action of the compounds according to the invention, it may be favorable to combine these compounds with a biguanide such as metformin, with an antidiabetic sulfonylurea, such as glyburide, glimepiride, tolbutamide, etc., a glucosidase inhibitor, a PPAR agonist, such as rosiglitazone, pioglitazone, etc., with an insulin product in a different administration form, with a DB4 inhibitor, with an insulin sensitizer or with meglitinide.

In addition to the acute antidiabetic effects, the compounds of formula I counteract the development of late complications of diabetes, and they can therefore be used as medicaments for the prevention and treatment of diabetic late damage, such as diabetic nephropathy, diabetic neuropathy, diabetic retinopathy, diabetic cardiomyopathy and other disorders which occur as a result of diabetes. In this connection, they can be combined advantageously with the antidiabetic medicaments described above under the NIDDM treatment. A combination with a favorable administration form of insulin may be of particular importance.

In addition to the protective effects against acute ischemic events and subsequent likewise acute reperfusion events, the NHE inhibitors of formula I according to the invention also have direct therapeutically useful action against disorders and impairments of the entire mammalian organism which are associated with manifestations of the chronically progressing aging process and can also be independent of acute states of hypoperfusion, also occurring under normal, non-ischemic conditions. These pathological age-related manifestations, such as disease, illness and death, induced over the long time of aging, which are now accessible to treatment with NHE inhibitors, are disorders and disturbances caused to a substantial extent by age-related changes in vital organs and their function which become more and more important in the aging organism.

Disorders associated with age-related dysfunction and age-related symptoms of wear of organs are, for example, inadequate responsiveness and reactivity of the blood vessels to contraction and relaxation reactions. This age-related decline in vascular reactivity to constricting and relaxing stimuli, which are an essential process of the cardiovascular system and thus of life and health, can be significantly diminished or abolished by NHE inhibitors. An important function and a measure of the maintenance of vascular reactivity is the blocking or slowing of the age-related progression of endothelial dysfunction, which can be abolished highly significantly by NHE inhibitors. The compounds of formula I are thus outstandingly suitable for the treatment and prevention of the age-related progression of endothelial dysfunction, especially of intermittent claudication. Moreover, the compounds of formula I are thus outstandingly suitable for the treatment and prevention of cardiac insufficiency, of congestive heart failure (CHF), and for the treatment and in particular for the prevention of age-related types of cancer.

Consideration may likewise be given to combination with hypotensive medicaments, such as with ACE inhibitors, angiotensin receptor antagonists, diuretics, $Ca^{2+}$ antagonists, etc., or with metabolism-normalizing medicaments, such as cholesterol-lowering agents. The compounds of formula I are thus suitable for the prevention of age-related tissue changes and for prolonging life while maintaining a high quality of life.

The compounds of the invention are effective inhibitors of the cellular sodium/proton antiporter (Na/H exchanger) which, in numerous disorders (essential hypertension, atherosclerosis, diabetes, etc.), is also elevated in cells which are easily amenable to measurements, such as, for example, in erythrocytes, platelets or leukocytes. The compounds used according to the invention are therefore suitable as excellent and simple scientific tools, for example in their use as diagnostic aids for the determination and differentiation of particular types of hypertension, but also of atherosclerosis, of diabetes and of late complications of diabetes, of proliferative disorders, etc.

NHE3 inhibitors are furthermore suitable for treating disorders (human and veterinary) caused by bacteria and by protozoa. In the case of disorders caused by protozoa, particular mention may be made of malaria diseases of man and of coccidiosis in poultry.

Moreover, the compounds are suitable as agents for controlling sucking parasites in human and veterinary medicine and in crop protection. Here, the use as an agent against blood-sucking parasites in human and veterinary medicine is preferred.

The compounds of the formula I are characterised apart from their potent NHE inhibition values, their pharmacological properties and the absence of unwanted biological effects also by favorable pharmacokinetic properties, which let their use as medicaments appear particularly favorable.

The invention thus relates to medicaments for human, veterinary or phytoprotective use which comprise an effective amount of a compound of formula I and/or a pharmaceutically acceptable salt thereof alone or in combination with other pharmacologically active compounds or medicaments.

Medicaments comprising a compound I can be administered, for example, orally, parenterally, intramuscularly, intravenously, rectally, nasally, by inhalation, subcutaneously or by suitable transcutaneously administration with the preferred administration being dependent on the particular appearance of the disorder. Here, the compounds I can be used alone or together with pharmaceutical excipients, both in veterinary medicine and in human medicine and in crop protection.

Excipients suitable for the desired pharmaceutical formulation are familiar to the skilled worker on the basis of his expert knowledge. Besides solvents, gel formers, suppository bases, tablet excipients and other active ingredient carriers, it is possible to use, for example, antioxidants, dispersants, emulsifiers, antifoams, masking flavors, preservatives, solubilizers or colorants.

For a form for oral use, the active compounds are mixed with the additives suitable for this purpose, such as carriers, stabilizers or inert diluents, and converted by conventional methods into suitable dosage forms such as tablets, coated tablets, two-piece capsules, aqueous, alcoholic or oily solutions. Examples of inert carriers which can be used are gum arabic, magnesia, magnesium carbonate, potassium phosphate, lactose, glucose or starch, especially corn starch. Preparation can moreover take place both as dry and as wet granules. Examples of suitable oily carriers or solvents are vegetable or animal oils such as sunflower oil or fish liver oil.

For subcutaneous, percutaneous or intravenous administration, the active compounds used are converted into a solution, suspension or emulsion, if desired with the substances customary for this purpose, such as solubilizers, emulsifiers or other excipients. Examples of suitable solvents are: water, physiological saline or alcohols, for example ethanol, propanol, glycerol, and also sugar solutions, such as glucose or mannitol solutions, or else a mixture of the various solvents mentioned.

Suitable as pharmaceutical formulation for administration in the form of aerosols or sprays are, for example, solutions, suspensions or emulsions of the active compound of formula I in a pharmaceutically acceptable solvent, such as, in particular, ethanol or water, or a mixture of such solvents.

The formulation may, if required, also comprise other pharmaceutical excipients such as surfactants, emulsifiers and stabilizers, and a propellant gas. Such a preparation normally contains the active compound in a concentration of about 0.1 to 10, in particular of about 0.3 to 3% by weight.

The dosage of the active compound of formula I to be administered and the frequency of administration depend on the potency and duration of action of the compounds used; also on the nature and severity of the disease to be treated, and on the sex, age, weight and individual response of the mammal to be treated.

On average, the daily dose of the compound of formula I for a patient weighing about 75 kg is at least 0.001 mg/kg, preferably 0.1 mg/kg, up to a maximum of 30 mg/kg, preferably 1 mg/kg, of body weight. For acute situations, for example immediately after suffering apnea in high mountain regions, it may even be necessary for the dosages to be higher. Especially on i.v. use, for example for an infarct patient in an intensive care unit, up to 200 mg/kg per day may be necessary. The daily dose can be divided into one or more, for example up to 4, individual doses.

The various features of novelty which characterize the invention are pointed out with particularity in the claims annexed to and forming a part of this disclosure. For a better understanding of the invention, its operating advantages, and specific objects attained by its use, reference should be made to the following description in which there are illustrated and described preferred embodiments of the invention.

DETAILED DESCRIPTION OF THE PREFERRED EMBODIMENTS

For the purpose of describing the specific compounds of the present invention, it is understood that if the compounds are enantiomerically pure, the configuration and/or the sign of the optical rotation is given, and if these data are missing, the compounds are racemates or not optically active.

The retention times (Rt) given below refer to LCMS measurements with the following parameters:

Analytical Methods:

A stationary phase: Merck Purospher 3μ 2×55 mm
mobile phase: 95% $H_2O$ (0.1% HCOOH)→95% acetonitrile (0.1% HCOOH); 5 min→95% acetonitrile (0.1% HCOOH); 2 min→95% $H_2O$ (0.1% HCOOH); 1 min; 0.45 ml/min.

B stationary phase: YMC J'sphere H80 ~4μ 2.1×33 mm
mobile phase: 95% $H_2O$ (0.1% HCOOH)→95% acetonitrile (0.08% HCOOH); 2.5 min→95% acetonitrile (0.08% HCOOH); 0.5 min→95% $H_2O$ (0.1% HCOOH); 0.5 min; 1.3 ml/min.

C stationary phase: YMC J'sphere H80 2×33 mm, 4μ, 2.1×20 mm
mobile phase: 90% $H_2O$ (0.05% TFA)→95% acetonitrile; 1.9 min; →95% acetonitrile 0.5 min; 1 ml/min.

D stationary phase: Merck Purospher 3μ 2×55 mm
mobile phase: 95% $H_2O$ (0.1% HCOOH)→95% acetonitrile (0.1% HCOOH); 3.4 min→95% acetonitrile (0.1% HCOOH); 1 min→95% $H_2O$ (0.1% HCOOH); 0.2 min; 0.75 ml/min.

E stationary phase: Merck Purospher 3μ 2×55 mm
mobile phase: 95% $H_2O$ (0.05% CF3COOH)→95% acetonitrile (0.05% CF3COOH); 3.4 min→95% acetonitrile (0.05% CF3COOH); 1 min; 0.75 ml/min.

F stationary phase: YMC J'sphere H80, 4μ, 2.1×20 mm
mobile phase: 96% $H_2O$ (0.05% CF3COOH)→95% acetonitrile; 2 min; →95% acetonitrile 0.4 min; 1 ml/min.

Preparative HPLC was carried out under the following conditions:
stationary phase: Merck Purospher RP18 (10 μM) 250×25 mm
mobile phase: 90% $H_2O$ (0.05% TFA)→90% acetonitrile; 40 min; 25 ml/min Example 1

3N-(5-Fluoro-2-benzimidazolyl)-4-methyl-3-thienylamine hydrochloride

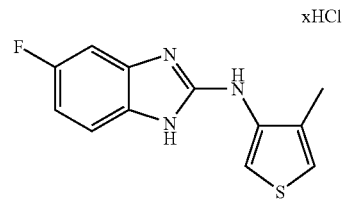

a) 4-Methyl-3-thienyl isothiocyanate is obtained by reacting equimolar amounts of 3-amino-4-methylthiophene and N,N'-thiocarbonyldiimidazole in anhydrous tetrahydrofuran (THF) by stirring the reaction mixture at room temperature for 5 hours and then allowing the mixture to stand at room temperature overnight. 4-Methyl-3-thienyl isothiocyanate is isolated by distillative removal of the solvent under reduced pressure using a rotary evaporator, dissolving the residue in ethyl acetate and washing the organic phase repeatedly with water. The organic phase is dried over sodium sulfate and the organic solvent is then distilled off under reduced pressure using a rotary evaporator, giving 4-methyl-3-thienyl isothiocyanate as a brown oily residue. 4-Methyl-3-thienyl isothiocyanate can be used without further purification.

b) N-(2-Amino-5-fluorophenyl)-N'-(4-methyl-3-thienyl)thiourea 0.02 mol of 4-fluoro-1,2-diaminobenzene is added to a solution of 0.02 mol of 4-methyl-3-thienyl isothiocyanate in 60 ml of anhydrous THF. The reaction mixture is stirred at room temperature for 2 hours and then allowed to stand overnight, and the solvent is then distilled off under reduced pressure using a rotary evaporator and the oily residue is purified on a silica gel column using a mixture of identical proportions of toluene and ethyl acetate.

Brown crystalline solid. M.p. 180° C.

c) 3N-(5-Fluoro-2-benzimidazolyl)-4-methyl-3-thienylamine hydrochloride

A molar excess (about 1.5 to 4 mol) of methyl iodide is added to 1.5 g (0.0053 mol) of N-(2-amino-5-fluorophenyl)-N'-(4-methyl-3-thienyl)thiourea in 50 ml of anhydrous ethanol, and the mixture is boiled at reflux for 5 hours. The mixture is allowed to stand at room temperature overnight and the ethanol is then distilled off under reduced pressure using a rotary evaporator, water is added to the residue and the pH is adjusted to 8-9 using saturated aqueous sodium bicarbonate solution. The mixture is extracted repeatedly with ethyl acetate, the organic phase is washed with water and dried over sodium sulfate, the solvent is distilled off under reduced pressure using a rotary evaporator and the residue is purified by silica gel column chromatography using a solvent mixture of identical proportions of ethyl acetate and toluene (hereinbelow referred to as "mixture 2") as mobile phase. The oily product obtained after distillative removal of the organic solvent is dissolved in ethyl acetate and made highly acidic using a saturated solution of hydrogen chloride in dry diethyl ether, and the precipitate that crystallizes out is, after relatively long standing, filtered off. Crystalline solid, m.p. 192+/−2° C.

Example 2

2-Chloro-3N-(5-fluoro-2-benzimidazolyl)-4-methyl-3-thienylamine hydrochloride and 2,5-dichloro-3N-(5-fluoro-2-benzimidazolyl)-4-methyl-3-thienylamine hydrochloride

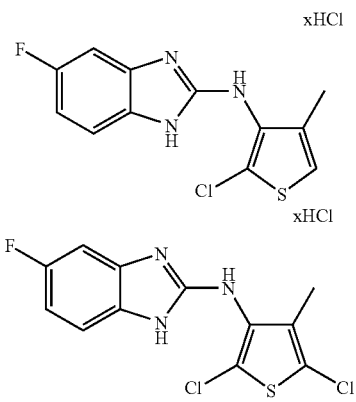

A solution of 0.24 g (0.0018 mol) of N-chlorosuccinimide in 15 ml of glacial acetic acid is added dropwise to a solution of 0.5 g (0.0018 mol) of 3N-(5-fluoro-2-benzimidazolyl)-4-methyl-3-thienylamine hydrochloride in 25 ml of glacial acetic acid, the reaction mixture is stirred at room temperature for about 2 to 3 hours and the solvent is distilled off under reduced pressure using a rotary evaporator. Water is added to the residue and the mixture is then made alkaline using 2N NaOH and extracted with ethyl acetate, the organic phase is washed with water and dried over sodium sulfate and the solvent is distilled off under reduced pressure using a rotary evaporator. The resulting oily residue is, by medium pressure column chromatography, using a solvent mixture of 20 parts of ethyl acetate, 10 parts of n-heptane and 3 parts of glacial acetic acid (hereinbelow referred to as "mixture 17") as mobile phase, separated and treatment with a solution of hydrogen chloride gas gives:

2-chloro-3N-(5-fluoro-2-benzimidazolyl)-4-methyl-3-thienylamine hydrochloride from fraction 1 and 2: colorless to slightly yellowish crystalline product, m.p. 200-202° C., 2,5-dichloro-3N-(5-fluoro-2-benzimidazolyl)-4-methyl-3-thienylamine hydrochloride from fraction 3: colorless to slightly yellowish crystalline product, m.p. 286-288° C.

Example 3

3N-(5,6-Dichloro-2-benzimidazolyl)-4-methyl-3-thienylamine hydrochloride

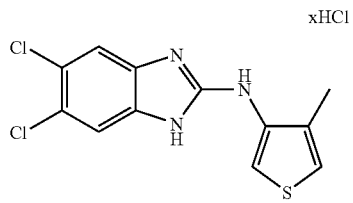

a) N-(2-Amino-4,5-dichlorophenyl)-N'-(4-methyl-3-thienyl)thiourea is obtained analogously to the reaction described in example 1 b) from 4-methyl-3-thienyl isothiocyanate and 4,5-dichloro-1,2-diaminobenzene. Crystalline solid, m.p. 310-320° C.

b) 3N-(5,6-Dichloro-2-benzimidazolyl)-4-methyl-3-thienylamine hydrochloride is obtained analogously to the procedure described in example 1 c) from N-(2-amino-4,5-dichlorophenyl)-N'-(4-methyl-3-thienyl)thiourea and methyl iodide. Crystalline solid, m.p. 290-294° C.

Example 4

3N-(2-Benzimidazolyl)-4-methyl-3-thienylamine hydrochloride

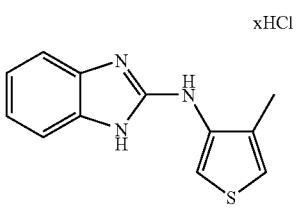

a) N-(2-Aminophenyl)-N'-(4-methyl-3-thienyl)thiourea is obtained analogously to the reaction described in example 1 b) from 4-methyl-3-thienyl isothiocyanate and 1,2-diaminobenzene. Crystalline solid having a 1st m.p. of 177-182° C., followed by another crystallization and 2nd m.p. 285-290° C.

b) 3N-(2-Benzimidazolyl)-4-methyl-3-thienylamine hydrochloride is obtained analogously to the procedure described in example 1 c) from N-(2-aminophenyl)-N'-(4-methyl-3-thienyl)thiourea and methyl iodide.

Crystalline solid following recrystallization from ethyl acetate/ethanol, m.p. 194-200° C.

Example 5

3N-(-4-Fluoro-2-benzimidazolyl)-4-methyl-3-thienylamine hydrochloride

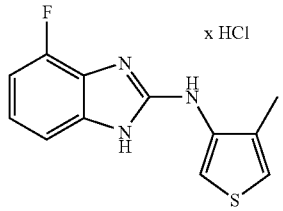

a) 3-Fluoro-1,2-diaminobenzene is obtained as an oily amorphous product by hydrogenation of 3-fluoro-2-nitrophenyl hydrazine (prepared by reaction of 2,6-difluoronitrobenzene with hydrazine hydrate) using hydrogen and 10% palladium on carbon catalyst in methanol at room temperature and atmospheric pressure.

b) N-(2-Amino-3-fluorophenyl)-N'-(4-methyl-3-thienyl)thiourea is obtained analogously to the reaction described in example 1 b) from 4-methyl-3-thienyl isothiocyanate and 3-fluoro-1,2-diaminobenzene. Crystalline solid, point of decomposition >240° C.

c) 3N-(-4-Fluoro-2-benzimidazolyl)-4-methyl-3-thienylamine hydrochloride is obtained analogously to the procedure described in example 1 c) from N-(2-amino-3-fluorophenyl)-N'-(4-methyl-3-thienyl)thiourea and methyl iodide. Amorphous precipitate which crystallizes under acetone. Crystalline solid, m.p. 220-230° C.

Example 6

3N-(4,6-Difluoro-2-benzimidazolyl)-4-methyl-3-thienylamine hydrochloride

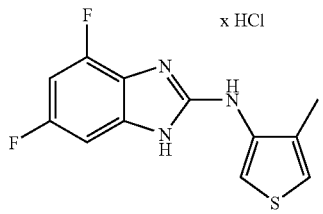

a) N-(2-Amino-3,5-difluorophenyl)-N'-(4-methyl-3-thienyl)thiourea is obtained analogously to the reaction described in example 1 b) from 4-methyl-3-thienyl isothiocyanate and 3,5-difluoro-1,2-diaminobenzene. Crystalline solid, 1st melting point: 178-182° C., another crystallization with 2nd m.p.: 299-301° C.

b) 3N-(4,6-Difluoro-2-benzimidazolyl)-4-methyl-3-thienylamine hydrochloride is obtained analogously to the procedure described in example 1 c) from N-(2-amino-3,5-difluorophenyl)-N'-(4-methyl-3-thienyl)thiourea and methyl iodide. Amorphous precipitate which crystallizes under ethyl acetate. Crystalline solid, m.p. 232-234° C.

Example 7

3N-(4,5,6,7-Tetrafluoro-2-benzimidazolyl)-4-methyl-3-thienylamine hydrochloride

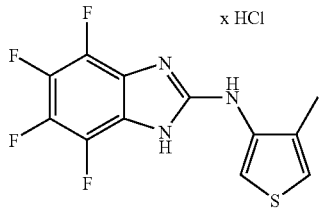

a) N-(2-Amino-3,4,5,6-tetrafluorophenyl)-N'-(4-methyl-3-thienyl)thiourea is obtained analogously to the reaction described in example 1 b) from 4-methyl-3-thienyl isothiocyanate and 3,4,5,6-tetrafluoro-1,2-diaminobenzene. Crystalline solid, m.p.: 286-290° C.

b) 3N-(3,4,5,6-Tetrafluoro-2-benzimidazolyl)-4-methyl-3-thienylamine hydrochloride is obtained analogously to the procedure described in example 1 c) from N-(2-amino-3,4,5,6-tetrafluorophenyl)-N'-(4-methyl-3-thienyl)thiourea and methyl iodide. Amorphous precipitate which crystallizes under ethyl acetate. Crystalline solid, m.p. 225-228° C.

Example 8

3N-(4-Methyl-2-benzimidazolyl)-4-methyl-3-thienylamine hydrochloride

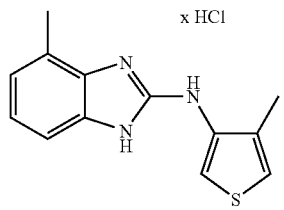

a) N-(2-Amino-3-methylphenyl)-N'-(4-methyl-3-thienyl)thiourea is obtained analogously to the reaction described in example 1 b) from 4-methyl-3-thienyl isothiocyanate and 3-methyl-1,2-diaminobenzene. Crystalline solid, m.p. 184-186° C., b) 3N-(4-Methyl-2-benzimidazolyl)-4-methyl-3-thienylamine hydrochloride is obtained analogously to the procedure described in example 1 c) from N-(2-amino-3-methylphenyl)-N'-(4-methyl-3-thienyl)thiourea and methyl iodide. Amorphous precipitate which crystallizes under acetone. Crystalline solid, point of decomposition: 320° C.

Example 9 trans-3N-(3a,4,5,6,7,7a-Hexahydro-1H-2-benzimidazolyl)-4-methyl-3-thienylamine hydrochloride (Racemate)

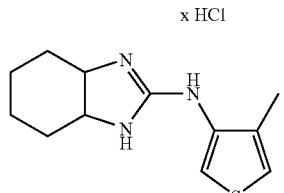

a) trans-N-(2-Aminocyclohexyl)-N'-(4-methyl-3-thienyl)thiourea (Racemate)

is obtained analogously to the reaction described in example 1 b) from 4-methyl-3-thienyl isothiocyanate and racemic trans-1,2-diaminocyclohexane. Crystalline solid, m.p. 205-210° C., b) trans-3N-(3a,4,5,6,7,7a-Hexahydro-1H-2-benz-
imidazolyl)-4-methyl-3-thienylamine hydrochloride
(Racemate)

0.6 g of racemic trans-N-(2-aminocyclohexyl)-N'-(4-methyl-3-thienyl)thiourea is suspended in 60 ml of toluene and dissolved by heating at 90° C. The mixture is allowed to cool to 70° C., a solution of 0.376 g of dicyclohexylcarbodiimide in 5 ml of anhydrous toluene is added dropwise and the mixture is stirred for a total of about 10 hours at 70° C. and for 2-3 days at room temperature. The crystalline solid is filtered off, the solvent is removed under reduced pressure using a rotary evaporator and the resulting oily residue is dissolved in a little ethyl acetate. Following addition of an anhydrous solution of hydrogen chloride in diethyl ether, a viscous precipitate is formed which, after addition of a little ethanol, crystallizes. Crystalline solid, m.p.: 261-264° C.

Example 10 trans-R,R-3N-(3a,4,5,6,7,7a-Hexahydro-1H-2-benz-
imidazolyl)-4-methyl-3-thienylamine hydrochloride

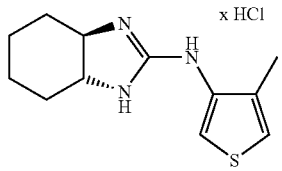

a) trans-R,R—N-(2-Aminocyclohexyl)-N'-(4-methyl-3-thienyl)thiourea is obtained analogously to the reaction described in example 1 b) from 4-methyl-3-thienyl isothiocyanate and trans-R,R-1,2-diaminocyclohexane by separation by silica gel column chromatography, eluting with a solvent mixture consisting of 10 parts of ethyl acetate, 5 parts of n-heptane, 5 parts of methylene chloride, 5 parts of methanol and 1 part of 26% strength aqueous ammonia (hereinbelow referred to as "mixture 4"), as an amorphous oily product in addition to a crystalline product having a higher molecular weight of m.p. 94-100° C.

The amorphous product is processed further without further purification.

b) trans-R,R—N-(3a,4,5,6,7,7a-Hexahydro-1H-2-benzimidazolyl)-4-methyl-3-thienylamine hydrochloride is obtained analogously to the procedure described in example 1 c) by reacting R,R—N-(2-aminocyclohexyl)-N'-(4-methyl-3-thienyl)thiourea and methyl iodide in anhydrous ethanol as solvent and reaction medium. Amorphous precipitate which is chromatographed on silica gel using mixture 4 as mobile phase and crystallized under acetone. Crystalline solid, m.p. 235-238° C.

Example 11 trans-S,S-3N-(3a,4,5,6,7,7a-Hexahydro-1H-2-benz-
imidazolyl)-4-methyl-3-thienylamine hydrochloride

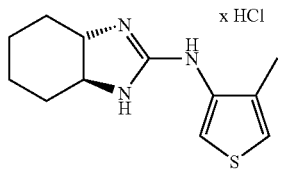

a) trans-S,S-3N-(2-Aminocyclohexyl)-N'-(4-methyl-3-thienyl)thiourea is obtained analogously to the reaction described in example 1 b) from 4-methyl-3-thienyl isothiocyanate and trans-S,S-1,2-diaminocyclohexane by separation by silica gel column chromatography using mixture 4 as mobile phase, as an amorphous oily product in addition to a product of higher molecular weight of m.p. 94-102° C.

The amorphous product is processed further without further purification.

b) trans-S,S—N-(3a,4,5,6,7,7a-Hexahydro-1H-2-benzimidazolyl)-4-methyl-3-thienylamine hydrochloride is obtained analogously to the procedure described in example 1 c) by reacting S,S—N-(2-aminocyclohexyl)-N'-(4-methyl-3-thienyl)thiourea and methyl iodide in anhydrous ethanol as solvent and reaction medium. Amorphous precipitate which is chromatographed on silica gel using mixture 4 as mobile phase and crystallizes under acetone. Crystalline solid, m.p. 225-230° C.

Example 12

2-Chloro-3N-(2-benzimidazolyl)-4-methyl-3-thienylamine hydrochloride and 2,5-dichloro-3N-(2-benzimidazolyl)-4-methyl-3-thienylamine hydrochloride

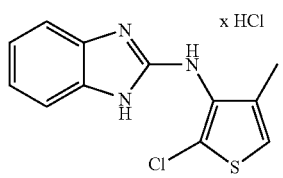

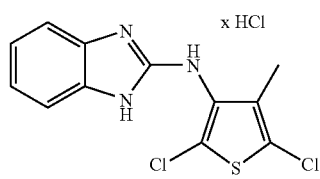

are obtained analogously to the procedure described in example 2 from 3N-(2-benzimidazolyl)-4-methyl-3-thienylamine hydrochloride and N-chlorosuccinimide in glacial acetic acid. Column chromatography on silica gel using mixture 17 as mobile phase results in the separation of 2,5-dichloro-3N-(2-benzimidazolyl)-4-methyl-3-thienylamine hydrochloride (colorless crystalline compound, m.p.: 291° C.) from 2-chloro-3N-(2-benzimidazolyl)-4-methyl-3-thienylamine hydrochloride (colorless crystalline compound, m.p. 257-259° C.).

Example 13

2-Chloro-3N-(4-methyl-2-benzimidazolyl)-4-methyl-3-thienylamine hydrochloride

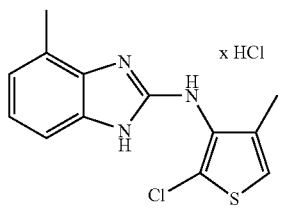

is obtained analogously to the procedure described in example 2 from 3N-(4-methyl-2-benzimidazolyl)-4-methyl-3-thienylamine hydrochloride and N-chlorosuccinimide in glacial acetic acid. Following column chromatography on silica gel using mixture 17 as mobile phase, 2-chloro-3N-(4-methyl-2-benzimidazolyl)-4-methyl-3-thienylamine hydrochloride is obtained as a colorless to slightly yellowish crystalline product. M.p. 255-259° C.

Example 14

2-Chloro-3N-(4,5,6,7-tetrafluoro-2-benzimidazolyl)-4-methyl-3-thienylamine hydrochloride

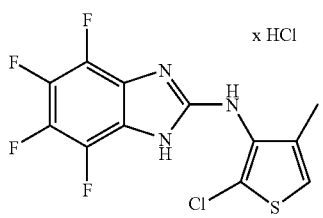

is obtained analogously to the procedure described in example 2: from 3N-(4,5,6,7-tetrafluoro-2-benzimidazolyl)-4-methyl-3-thienylamine hydrochloride and N-chlorosuccinimide in glacial acetic acid. Crystalline product. M.p. 233-235° C.

Example 15 trans-2-Chloro-3N-(3a,4,5,6,7,7a-hexahydro-1H-2-benzimidazolyl)-4-methyl-3-thienylamine hydrochloride (Racemate)

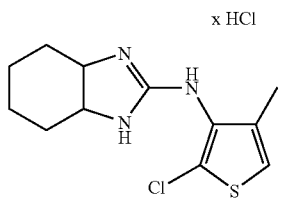

is obtained analogously to the procedure described in example 2: from 3N-(3a,4,5,6,7,7a-hexahydro-1H-2-benzimidazolyl)-4-methyl-3-thienylamine hydrochloride (racemate) and N-chlorosuccinimide in glacial acetic acid. Crystalline product. M.p. 258-260° C.

Example 16 trans-R,R-2-Chloro-3N-(3a,4,5,6,7,7a-hexahydro-1H-2-benzimidazolyl)-4-methyl-3-thienylamine hydrochloride and trans-R,R-2,5-dichloro-3N-(3a,4,5,6,7,7a-hexahydro-1H-2-benzimidazolyl)-4-methyl-3-thienylamine hydrochloride

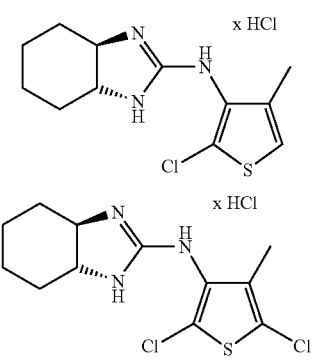

are obtained analogously to the procedure described in example 2: from trans-R,R-3N-(3a,4,5,6,7,7a-hexahydro-1H-2-benzimidazolyl)-4-methyl-3-thienylamine hydrochloride and N-chlorosuccinimide in glacial acetic acid following chromatographic separation of the two crystalline products in the following order:

a) trans-R,R-2,5-dichloro-3N-(3a,4,5,6,7,7a-hexahydro-1H-2-benzimidazolyl)-4-methyl-3-thienylamine hydrochloride, decomposition with foaming starting at 80° C., b) trans-R,R-2-chloro-3N-(3a,4,5,6,7,7a-hexahydro-1H-2-benzimidazolyl)-4-methyl-3-thienylamine hydrochloride, crystalline product. M.p. 260-262° C.

Example 17 trans-S,S-2-Chloro-3N-(3a,4,5,6,7,7a-hexahydro-1H-2-benzimidazolyl)-4-methyl-3-thienylamine hydrochloride

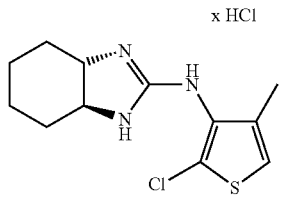

is obtained analogously to the procedure described in example 2: from trans-S,S-3N-(3a,4,5,6,7,7a-hexahydro-1H-2-benzimidazolyl)-4-methyl-3-thienylamine hydrochloride and N-chlorosuccinimide in glacial acetic acid following chromatographic separation. Colorless crystalline product, m.p. 258-260° C.

Example 18

2-Bromo-3N-(2-benzimidazolyl)-4-methyl-3-thienylamine hydrochloride and 2,5-dibromo-3N-(2-benzimidazolyl)-4-methyl-3-thienylamine hydrochloride

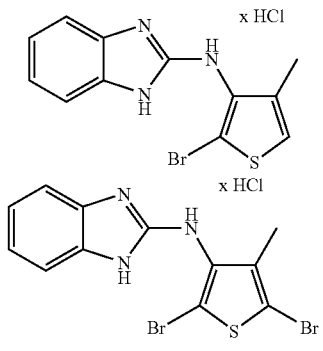

are obtained analogously to the procedure described in example 2: from 3N-(2-benzimidazolyl)-4-methyl-3-thienylamine hydrochloride and N-bromosuccinimide (instead of N-chlorosuccinimide) in glacial acetic acid. Following column chromatography on silica gel using a mixture of 5 parts of dichloromethane, 3 parts of n-heptane, 1 part of glacial acetic acid and 1 part of ethanol (hereinbelow referred to as "mixture 1") as mobile phase and treatment with a solution of hydrogen chloride gas in ether, 2-bromo-3N-(2-benzimidazolyl)-4-methyl-3-thienylamine hydrochloride, a crystalline product of m.p. 228-231° C., and 2,5-dibromo-3N-(2-benzimidazolyl)-4-methyl-3-thienylamine hydrochloride, a crystalline product of m.p. 208-210° C., are obtained by fractional crystallization in ethyl acetate.

Example 19 trans-R,R-2-Bromo-3N-(3a,4,5,6,7,7a-hexahydro-1H-2-benzimidazolyl)-4-methyl-3-thienylamine hydrochloride and trans-R,R-2,5-dibromo-3N-(3a,4,5,6,7,7a-hexahydro-1H-2-benzimidazolyl)-4-methyl-3-thienylamine hydrochloride

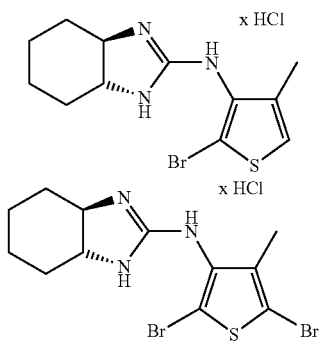

are obtained analogously to the procedure described in example 19: from trans-R,R-3N-(3a,4,5,6,7,7a-hexahydro-1H-2-benzimidazolyl)-4-methyl-3-thienylamine hydrochloride and N-bromosuccinimide in glacial acetic acid. Following column chromatography on silica gel using mixture 1 as mobile phase, and treatment with a solution of hydrogen chloride gas in ether, trans-R,R-2-bromo-3N-(3a,4,5,6,7,7a-hexahydro-1H-2-benzimidazolyl)-4-methyl-3-thienylamine hydrochloride, crystalline product, m.p. 215-218° C. and trans-R,R-2,5-dibromo-3N-(3a,4,5,6,7,7a-hexahydro-1H-2-benzimidazolyl)-4-methyl-3-thienylamine hydrochloride, crystalline product, m.p. 218-220° C. are obtained following fractional crystallization in ethyl acetate.

Example 20

3N-(4-Chloro-2-benzimidazolylamino)-4-methylthiophene hydrochloride

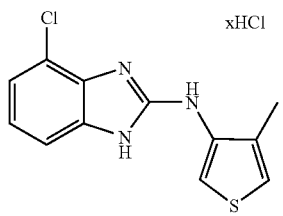

a) N-(2-Amino-3-chlorophenyl)-N'-(4-methyl-3-thienyl)thiourea is obtained analogously to the reaction described in example 1 b) from 4-methyl-3-thienyl isothiocyanate and 3-chloro-1,2-diaminobenzene (prepared by catalytic hydrogenation of 3-chloro-2-nitroaniline using Pt on activated carbon under atmospheric pressure at room temperature). Crystalline solid, m.p. 298-305° C., b) 3N-(4-Chloro-2-benzimidazolylamino)-4-methylthiophene hydrochloride is obtained analogously to the procedure described in example 1 c) from N-(2-amino-3-chlorophenyl)-N'-(4-methyl-3-thienyl)-thiourea and methyl iodide. Amorphous precipitate which crystallizes under ethyl acetate. Crystalline solid, point of decomposition 240-245° C.

Example 21

2-Chloro-3N-(4-chloro-2-benzimidazolylamino)-4-methylthiophene hydrochloride

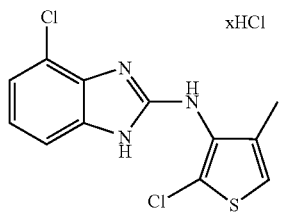

is obtained analogously to the procedure described in example 2 from 3N-(4-chloro-2-benzimidazolyl)-4-methyl-3-thienylamine hydrochloride and N-chlorosuccinimide in glacial acetic acid. Following silica gel column chromatography using a mixture of 10 parts of methylene chloride and 1 part of methanol as mobile phase, 2-chloro-3N-(4-chloro-2-benzimidazolylamino)-4-methylthiophene hydrochloride is, after crystallization under ethyl acetate, obtained as a colorless to slightly yellowish solid. M.p. 270-272° C.

Example 22

2-Bromo-3N-(4-chloro-2-benzimidazolylamino)-4-methylthiophene hydrochloride

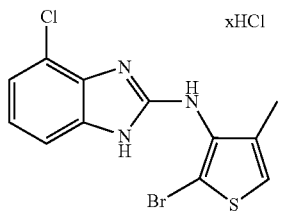

is obtained analogously to the procedure described in example 2 from 3N-(4-chloro-2-benzimidazolylamino)-4-methylthiophene hydrochloride and N-bromosuccinimide (instead of N-chlorosuccinimide) in glacial acetic acid. Following silica gel column chromatography using a mixture of 20 parts of ethyl acetate, 10 parts of n-heptane and 3 parts of glacial acetic acid as mobile phase and treatment with a solution of hydrogen chloride gas in ether, 2-bromo-3N-(4-chloro-2-benzimidazolylamino)-4-methylthiophene hydrochloride is obtained by fractionated crystallization in ethyl acetate in the presence of hydrogen-chloride-saturated ether. Crystalline product of m.p. 278-280° C.

Example 23

(2-Bromo-4-methylthiophene-3-yl)-(5-fluoro-1H-benzoimidazol-2-yl)amine hydrochloride

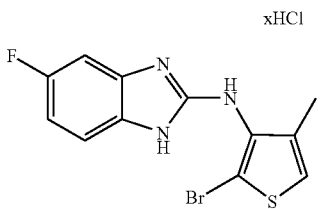

(5-Fluoro-1H-benzimidazol-2-yl)-(4-methylthiophene-3-yl)amine (300 mg) (example 1) was dissolved in glacial acetic acid (50 ml). At room temperature, N-bromosuccinimide (207 mg) dissolved in glacial acetic acid (10 ml), was slowly added dropwise, with vigorous stirring. After the addition had ended, stirring was continued for another 10 min and the glacial acetic acid was then distilled off under reduced pressure, and the residue was dissolved in ethyl acetate and washed with saturated potassium carbonate solution. The organic phase was dried over magnesium sulfate, filtered and concentrated. The residue was purified by preparative chromatography and the product-containing fractions were combined, freed from acetonitrile, made basic and extracted three times with ethyl acetate. The organic phases were combined, dried (MgSO$_4$) and filtered. Following removal of the solvent under reduced pressure, water and 2N hydrochloric acid were added to the residue and the mixture was freeze-dried. This gave 245 mg of the desired product.

LCMS-Rt (B): 0.95 min
MS (ES$^+$, M+H$^+$): 326.09

Example 24

2-Bromo-3N-(4-fluoro-2-benzimidazolylamino)-4-methylthiophene Hydrochloride and 2,5-dibromo-3N-(4-fluoro-2-benzimidazolylamino)-4-methylthiophene hydrochloride

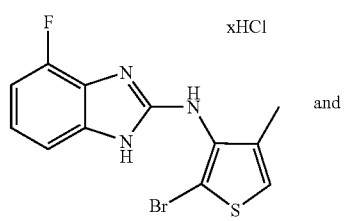

and

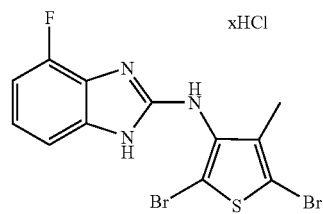

A solution of 0.161 g of N-bromosuccinimide in 6 ml of glacial acetic acid is added to a solution of 0.214 g of 3N-(4-fluoro-2-benzimidazolylamino)-4-methylthiophene hydrochloride in 6 ml of glacial acetic acid, and the mixture is stirred at room temperature for 30 minutes. After removal of the solvent by distillation, water is added to the residue and the mixture is made alkaline using 2N NaOH and extracted with ethyl acetate. The organic phase is dried, the solvent is distilled off and the residue is separated by silica gel column chromatography using a mixture of 20 parts of ethyl acetate, 10 parts of n-heptane and 3 parts of glacial acetic acid. The hydrochlorides of the two compounds are obtained by distilling off the fractionated solutions, dissolving the residue in ethyl acetate and precipitating the product by addition of hydrogen-chloride-saturated diethyl ether. Crystallization was promoted by gentle warming.

Example 24a

2-Bromo-3N-(4-fluoro-2-benzimidazolylamino)-4-methylthiophene hydrochloride: colorless crystals; m.p. 212° C. (decomposition)

Example 24b 2,5-Dibromo-3N-(4-fluoro-2-benzimidazolylamino)-4-methylthiophene hydrochloride: colorless crystals; m.p. 242-244° C. (decomposition)

Example 25

3N-(5-Methoxy-2-benzimidazolylamino)-4-methylthiophene

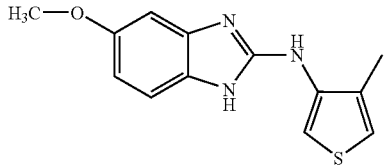

a) N-(2-Amino-4-methoxyphenyl)-N'-(4-methyl-3-thienyl)thiourea

A mixture of 5.89 g of 4-methylthiophene 3-isothiocyanate and 5 g of 4-methoxy-1,2-diaminobenzene in 60 ml of anhydrous THF is stirred at room temperature for 2 hours, and the solvent is distilled off. Water is added to the residue, the mixture is extracted with ethyl acetate, the dark solution is treated with activated carbon and the organic solvent is re-evaporated. With gentle warming, the residue is treated repeatedly with diisopropyl ether and the solid is filtered off. Brown crystalline solid, m.p. 143-146° C.

b) A mixture of 2.83 g of N-(2-amino-4-methoxyphenyl)-N'-(4-methyl-3-thienyl)thiourea, 8.5 g of methyl iodide, and 100 ml of anhydrous ethanol is boiled under reflux for 5 hours, and the solvent is then distilled off and water is added to the residue. Using 2N aqueous sodium hydroxide solution, the mixture is made alkaline and then extracted with ethyl acetate, the organic phase is treated with water and then with activated carbon and the product is purified by silica gel column chromatography using a mobile phase mixture of 20 parts of ethyl acetate, 10 parts of n-heptane and 3 parts of glacial acetic acid. This gives 3N-(5-methoxy-2-benzimidazolylamino)-4-methylthiophene as an amorphous product.

Example 26

3N-(5-Methoxy-2-benzimidazolylamino)-4-methylthiophene hydrochloride

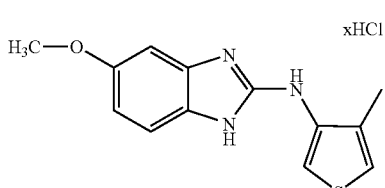

is obtained by precipitating a solution of 0.2 g of 3N-(5-methoxy-2-benzimidazolylamino)-4-methylthiophene (example 25) in 10 ml of ethyl acetate using a saturated solution of hydrogen chloride gas and diethyl ether, giving a crystalline precipitate. M.p.: 222-225° C.

Example 27

2-Chloro-3N-(5-methoxy-2-benzimidazolylamino)-4-methylthiophene hydrochloride

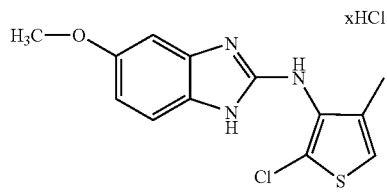

For about 2 to 2½ hours, a mixture of 0.519 g of 3N-(5-methoxy-2-benzimidazolylamino)-4-methylthiophene hydrochloride, 0.046 g of N-chlorosuccinimide and 10-15 ml of glacial acetic acid is heated at 45° C. The glacial acetic acid is then distilled off, water is added to the residue and the mixture is adjusted to pH 9-10 using 2N NaOH. The mixture is extracted with ethyl acetate, the solvent is evaporated and the residue is chromatographed on silica gel on a medium-pressure column using a mixture of 20 parts of ethyl acetate, 10 parts of n-heptane and 3 parts of glacial acetic acid. The base obtained after removal of the solvent by distillation is, in ethyl acetate, converted into the hydrochloride using saturated ethereal hydrogen chloride solution, and the product is crystallized under ethyl acetate. Crystalline solid m.p.: 182-186° C.

Example 28

2,5-Dichloro-3N-(5-methoxy-2-benzimidazolylamino)-4-methylthiophene hydrochloride

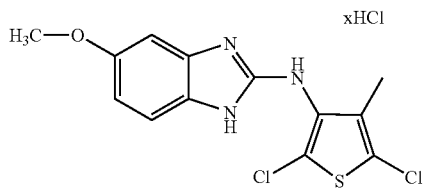

Analogous work-up of a reaction mixture of 3N-(5-methoxy-2-benzimidazolylamino)-4-methylthiophene hydrochloride, N-chlorosuccinimide and glacial acetic acid for about 2 to 2½ hours at 55° C. gave 2,5-dichloro-3N-(5-methoxy-2-benzimidazolylamino)-4-methylthiophene. Crystalline solid, m.p.: 278-282° C.

Example 29

3N-(4-Methoxy-2-benzimidazolylamino)-4-methylthiophene hydrochloride

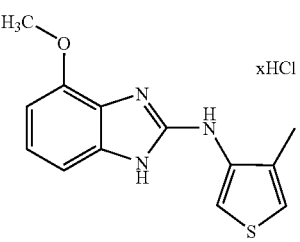

a) 3-Methoxy-1,2-Diaminobenzene was obtained as a brown oil by hydrogenation of 2-methoxy-6-nitroaniline using hydrogen gas and Raney nickel as catalyst at room temperature and a pressure of 3 bar. The product was converted into the thiourea without further purification.

b) N-(2-Amino-3-methoxyphenyl)-N'-(4-methyl-3-thienyl)thiourea is obtained analogously to the procedure described in example 25 a) from 3-methoxy-1,2-diaminobenzene and 4-methyl-3-thienyl isothiocyanate in anhydrous THF, followed by medium-pressure chromatography on silica gel using a mixture of 1 part of toluene and 1 part of ethyl acetate. Crystalline solid, m.p.: 148-153° C. Solidification of the melt and next m.p. at 260° C.

c) 3N-(4-Methoxy-2-benzimidazolylamino)-4-methylthiophene hydrochloride is obtained analogously to the procedures described in examples 25 and 26 from N-(2-amino-3-methoxyphenyl)-N'-(4-methyl-3-thienyl)thiourea by heating with methyl iodide in THF, analogous work-up and treatment of the benzimidazole with HCl in ether. Crystalline solid, m.p.: 230-235° C.

Example 30

2-Chloro-3N-(4-methoxy-2-benzimidazolylamino)-4-methylthiophene hydrochloride

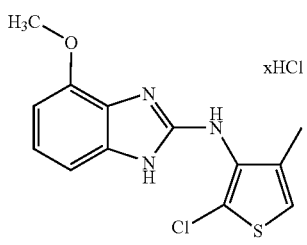

A mixture of 0.1 g of 3N-(4-methoxy-2-benzimidazolylamino)-4-methylthiophene hydrochloride, 0.046 g of N-chlorosuccinimide and 10-15 ml of glacial acetic acid is heated at 40° C. for about 2 to 2½ hours. The glacial acetic acid is then distilled off, water is added to the residue and the pH is adjusted to 9-10 using 2N NaOH. The mixture is extracted with ethyl acetate, the solvent is evaporated and the residue is chromatographed on silica gel on a medium-pressure column using a mixture of 20 parts of ethyl acetate, 10 parts of n-heptane and 3 parts of glacial acetic acid. The resulting base is, in ethyl acetate, converted into the hydrochloride using saturated ethereal hydrogen chloride solution. Colorless to light-yellow crystalline solid, m.p.: 248-250° C.

Example 31

3N-(4-Chloro-6-trifluoromethyl-2-benzimidazolylamino)-4-methylthiophene hydrochloride

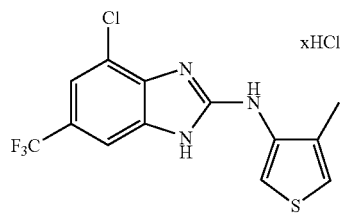

a) N-(2-Amino-3-chloro-5-trifluoromethylphenyl)-N'-(4-methyl-3-thienyl)thiourea is obtained analogously to the procedure described in example 25 a) by reacting 3-chloro-5-trifluoromethyl-1,2-diaminobenzene and 4-methyl-3-thienyl isothiocyanate in anhydrous THF at room temperature for 3 days. The solvent is distilled off and water is added to the residue, and the mixture is then extracted with ethyl acetate, the solvent is again distilled off and the amorphous residue is crystallized under diisopropyl ether. M.p.: >310° C.

b) 3N-(4-chloro-6-trifluoromethyl-2-benzimidazolylamino)-4-methylthiophene hydrochloride is obtained analogously to the procedures described under examples 25 and 26 from N-(2-amino-3-chloro-5-trifluoromethylphenyl)-N'-(4-methyl-3-thienyl)thiourea by boiling with methyl iodide in THF under reflux conditions for 5 hours, analogous work-up and purification by medium-pressure silica gel column chromatography using a mixture of identical parts by volume of ethyl acetate and toluene. The solvent is evaporated and the residue is then dissolved in ethyl acetate, giving, by addition of a saturated solution of hydrogen chloride in diethyl ether, 3N-(4-chloro-6-trifluoromethyl-2-benzimidazolylamino)-4-methylthiophene hydrochloride as a crystalline precipitate. Solid, m.p.: 210-213° C.

Example 32

2-Chloro-3N-(4-chloro-6-trifluoromethyl-2-benzimidazolylamino)-4-methylthiophene hydrochloride

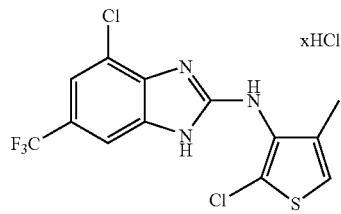

A mixture of 0.34 g of 3N-(4-methoxy-2-benzimidazolylamino)-4-methylthiophene hydrochloride, 0.151 g of N-chlorosuccinimide and 20 ml of glacial acetic acid is stirred at room temperature for ½ hour and heated at 60° C. for one hour. The glacial acetic acid is then distilled off, water is added to the residue and the pH is adjusted to 9-10 using 2N NaOH. The mixture is extracted with ethyl acetate, the solvent is evaporated and the residue is chromatographed on silica gel on a medium-pressure column using a mixture of identical parts of toluene and ethyl acetate. The solvent is distilled off and the resulting base is then, in ethyl acetate, converted into the hydrochloride using saturated ethereal hydrogen chloride solution. Colorless to light-yellow crystalline solid. mp.: 247-250° C.

Example 33

3N-(4-Carboxy-2-benzimidazolylamino)-4-methylthiophene hydrochloride

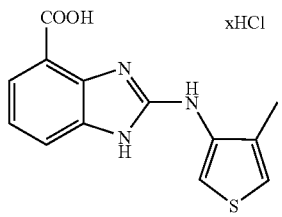

a) N-(2-Amino-3-carboxyphenyl)-N'-(4-methyl-3-thienyl)thiourea is obtained analogously to the procedure described in example 25 a) from 3-carboxy-1,2-diaminobenzene and 4-methyl-3-thienyl isothiocyanate in anhydrous THF, followed by medium-pressure chromatography on silica gel using a mixture of 12 parts of methylene chloride and 1 part of methanol. Amorphous product.

b) 3N-(4-Carboxy-2-benzimidazolylamino)-4-methylthiophene hydrochloride is obtained by boiling a solution of 1.12 g of N-(2-amino-3-carboxyphenyl)-N'-(4-methyl-3-thienyl)thiourea and 3.1 g of methyl iodide in 60 ml of ethanol under reflux. The solvent is evaporated, water is added to the residue, the pH is adjusted to 5 using 2N aqueous HCl and the precipitate is filtered off. Crystalline solid, point of decomposition: 265-285° C.

Example 34

2-Chloro-3N-(4-carboxy-2-benzimidazolylamino)-4-methylthiophene hydrochloride

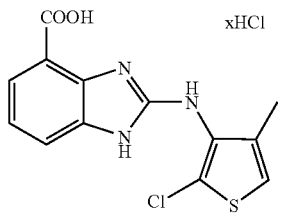

is obtained analogously to the procedure described in example 32 from 0.2 g of 3N-(4-carboxy-2-benzimidazolylamino)-4-methylthiophene hydrochloride and 0.103 g of N-chlorosuccinimide in 20-25 ml of glacial acetic acid and precipitation of the corresponding hydrochloride using HCl-saturated diethyl ether in ethyl acetate and subsequent crystallization under diisopropyl ether and ethyl acetate. Point of decomposition 170° C.

Example 35

3N-[4-(1-Piperidinocarbonyl)-2-benzimidazolylamino]-4-methylthiophene hydrochloride

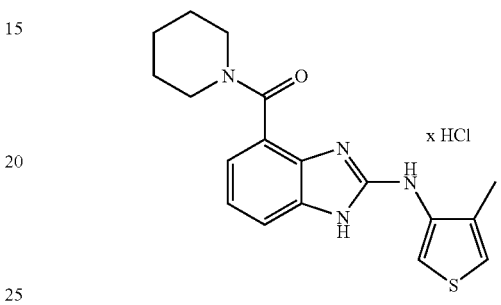

0.215 g of N,N'-carbonyldiimidazole is added to a mixture of 0.330 g of 3N-(4-carboxy-2-benzimidazolylamino)-4-methylthiophene hydrochloride, 30 ml of anhydrous THF and 5 ml of anhydrous dimethylacetamide. The mixture is stirred at room temperature for about 4 hours, when the evolution of carbon dioxide has ceased, and 0.411 g of piperidine is then added. The solution is stirred at room temperature for 2 hours and, after standing overnight, the solvent is distilled off under reduced pressure. The residue is triturated with water, the solid is filtered off and dissolved in ethyl acetate, the insoluble fraction is removed by filtration and the solvent is distilled off under reduced pressure. Foam-like amorphous product.

Example 36

2-Chloro-4-methyl-3N-[4-(1-piperidinocarbonyl)-2-benzimidazolylamino]-thiophene hydrochloride

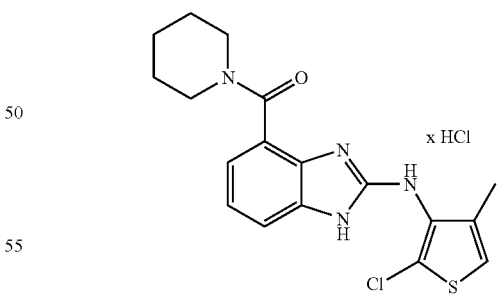

A mixture of 0.2 g of 3N-[4-(1-piperidinocarbonyl)-2-benzimidazolylamino]-4-methylthiophene hydrochloride and 0.086 g of N-chlorosuccinimide in about 20 ml of glacial acetic acid is stirred at room temperature for 1½ hours and at 35° C. for about 30 min, the solvent is distilled off and the residue is, after addition of water, made alkaline using 2N NaOH. Following extraction with ethyl acetate, the solvent is evaporated and the residue is purified by medium-pressure silica gel column chromatography using a mixture of 20 parts of ethyl acetate, 10 parts of n-heptane and 3 parts of glacial acetic acid. The solvent is distilled off, the residue is dissolved in ethyl acetate and the mixture is acidified using a solution of ether saturated with hydrogen chloride. The amorphous residue is crystallized under a mixture of ethyl acetate with a little acetone and a little ethanol. Amorphous solid, point of decomposition from 100° C.

Example 37

2-Chloro-3N-(4-fluoro-2-benzimidazolylamino)-4-methylthiophene hydrochloride

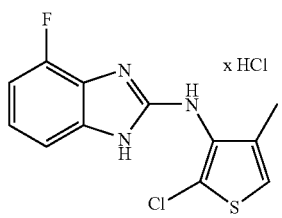

0.132 g of N-chlorosuccinimide is added to 0.234 g of 3N-(4-fluoro-2-benzimidazolylamino)-4-methylthiophene hydrochloride in about 20 ml of glacial acetic acid and the mixture is stirred at room temperature for 30 minutes and at 50-60° C. for another 1½ hours. The acetic acid is distilled off under reduced pressure, water is then added to the residue and the pH is adjusted to about 10-11 using 2N NaOH, and the mixture is extracted with ethyl acetate, which is then distilled off. The residue is chromatographed on a silica gel column under medium-pressure conditions using a mixture of 20 parts of ethyl acetate, 10 parts of n-heptane and 3 parts of glacial acetic acid. After concentration, the residue is dissolved in a little ethyl acetate and the hydrochloride is precipitated by addition of hydrogen-chloride-saturated diethyl ether. Colorless to light-yellow crystalline solid. M.p.: 268-270° C.

Example 38

2-Chloro-3N-(4-hydroxy-2-benzimidazolylamino)-4-methylthiophene hydrochloride

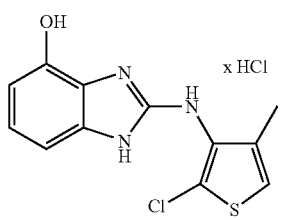

A suspension of 0.13 g of 2-chloro-3N-(4-methoxy-2-benzimidazolylamino)-4-methylthiophene hydrochloride in about 20 ml of anhydrous methylene chloride is added to a suspension of 0.29 g of activated anhydrous aluminum chloride in 10 ml of anhydrous methylene chloride, and the reaction mixture is stirred at 55° C. for 2 hours. After cooling, the reaction mixture is poured into ice-water and extracted with ethyl acetate, the organic phase is dried over sodium sulfate and the solvent is distilled off. The residue is chromatographed on a silica gel column under medium-pressure conditions using a mixture of 20 parts of ethyl acetate, 10 parts of n-heptane and 3 parts of glacial acetic acid, and the eluate is concentrated under reduced pressure. The residue is dissolved in ethyl acetate and the hydrochloride is precipitated by addition of hydrogen-chloride-saturated diethyl ether. Crystalline solid. M.p. 246-248° C.

Example 39

2-Chloro-3N-(2-benzimidazolylamino)-4-methylthiophene

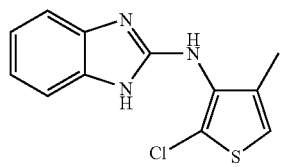

is obtained by adding 2N NaOH to a solution of 3 g of 2-chloro-3N-(2-benzimidazolylamino)-4-methylthiophene hydrochloride in 200 ml of water until a pH of 10 is set. The crystals are filtered off and washed repeatedly with water. Yield: 2.52 g. Colorless crystal powder. M.p. 182-185° C.

Example 40

2-Chloro-3N-(2-benzimidazolylamino)-4-methylthiophene hydrobromide

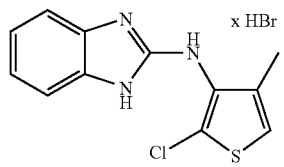

0.25 g of 2-chloro-3N-(2-benzimidazolylamino)-4-methylthiophene is dissolved in 10 ml of ethanol, 0.1 ml of 48% strength HBr is then added and the mixture is stirred at room temperature for a little while. The solvent is distilled off and the residue is crystallized under ethyl acetate. Yield: 0.29 g. Colorless crystals, point of decomposition: 252-254° C.

Example 41

2-Chloro-3N-(2-benzimidazolylamino)-4-methylthiophene Adipic Acid Salt

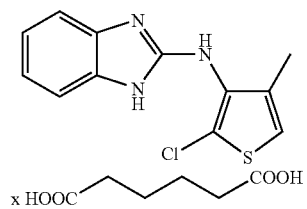

is obtained analogously to the procedure described in example 40 from 2-chloro-3N-(2-benzimidazolylamino)-4-methylthiophene using one equivalent of adipic acid. Colorless crystals. M.p. 155-157° C.

Example 42

2-Chloro-3N-(2-benzimidazolylamino)-4-methylthiophene Oxalic Acid Salt

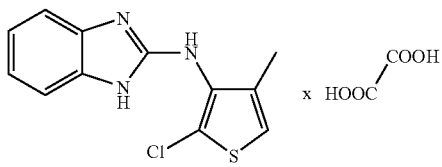

is obtained analogously to the procedure described in example 40 by reacting 2-chloro-3N-(2-benzimidazolylamino)-4-methylthiophene with one equivalent of oxalic acid in ethyl acetate. Colorless crystals. M.p.: 220-222° C.

Example 43

2-Chloro-3N-(2-benzimidazolylamino)-4-methylthiophene Phosphoric Acid Salt

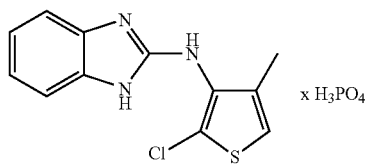

is obtained analogously to the procedure described in example 40 from 2-chloro-3N-(2-benzimidazolylamino)-4-methylthiophene using one equivalent of phosphoric acid. Colorless crystals. Decomposition range: 113-175° C.

Example 44

(1H-Benzimidazol-2-yl)-(2-chloro-4-methylthiophen-3-yl)methylamine

Finely powdered dry potassium carbonate (66 mg) was added to a solution of 2-chloro-3N-(2-benzimidazolyl)-4-methyl-3-thienylamine (125 mg, from example 39) and dry methanol (20 ml). Methyl iodide (74 mg) was then added dropwise with exclusion of moisture and vigorous stirring, and the mixture was kept under reflux for three days. The solvent was removed under reduced pressure and the residue was then partitioned between ethyl acetate and water, the ethyl acetate phase was dried with magnesium sulfate, the magnesium sulfate was filtered off and the filtrate was evaporated to dryness. The product was then purified by preparative HPLC. The product-containing fractions were combined and, after removing the acetonitrile under reduced pressure, freeze-dried. For further purification, the product was finally chromatographed on silica gel using ethyl acetate/heptane (1/4). The product-containing fractions were combined and then evaporated to dryness, and the residue was taken up in HCl and freeze-dried. This gave 5 mg of a solid.

LCMS-Rt (A): 2.04 min

MS (ES$^+$, M+H$^+$): 278.05

Example 45

(5,6-Difluoro-1H-benzimidazol-2-yl)-(4-methylthiophen-3-yl)amine trifluoroacetic acid salt

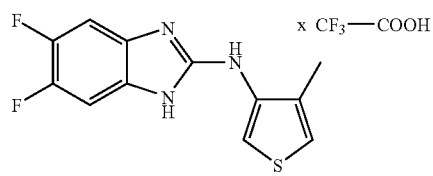

3-Isothiocyanato-4-methylthiophene (1.08 g), dissolved in absolute tetrahydrofuran (30 ml), was added dropwise to a solution of 1,2-diamino-4,5-difluorobenzene (1 g) in absolute tetrahydrofuran (20 ml). The mixture was then stirred at room temperature for 2 hours and allowed to stand overnight. Methyl iodide (0.44 ml) was added and the mixture was then stirred for 8 hours and allowed to stand overnight. The tetrahydrofuran was then removed under reduced pressure, the residue was partitioned between ethyl acetate and water, the phases were separated and the ethyl acetate phase was dried over magnesium sulfate. The residue was absorbed under silica gel and chromatographed on silica gel using the mobile phase n-heptane:ethyl acetate=1:1. This gave 229 mg of the desired compound as the free base.

An impure fraction from the above chromatography was purified by preparative HPLC. Following freeze-drying, 42.2 mg of the desired compound were isolated as trifluoroacetic acid salt.

LCMS-Rt (A): 1.98 min

MS (ES$^+$, M+H$^+$): 266.13

Example 46

(2-Chloro-4-methylthiophen-3-yl)-(5,6-difluoro-1H-benzoimidazol-2-yl)amine hydrochloride

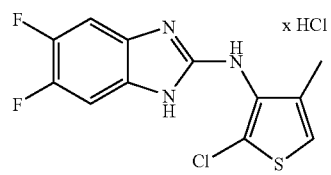

At room temperature, a solution of N-chlorosuccinimide (124.6 mg) in glacial acetic acid (5 ml) was added dropwise to a solution of (5,6-difluoro-1H-benzimidazol-2-yl)-(4-methylthiophen-3-yl)amine (225 mg) in glacial acetic acid (5 ml). The mixture was then stirred at room temperature for 3.5 hours. The glacial acetic acid was then removed and the residue was taken up in water and adjusted to pH 10 using 2 M aqueous sodium hydroxide solution. The aqueous phase was extracted three times with ethyl acetate, the combined organic phases were dried over magnesium sulfate and the solvent was removed. The residue was purified by preparative chromatography and the product-containing fractions were combined, freed from acetonitrile, made basic and extracted three times with ethyl acetate. The organic phases were combined, dried (MgSO₄), filtered and concentrated. The residue was taken up in water, acidified with 10% strength hydrochloric acid and freeze-dried. This gave 81 mg of the desired product as a solid.

LCMS-Rt (A): 2.15 min

MS (ES⁺, M+H⁺): 300.11

Example 47

(2-Bromo-4-methylthiophen-3-yl)-(5,6-difluoro-1H-benzoimidazol-2-yl)-amine

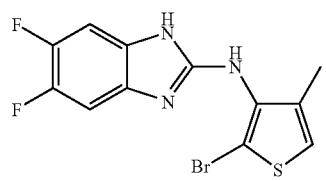

At room temperature, a solution of N-bromosuccinimide (8 mg) in glacial acetic acid (0.5 ml) was added dropwise to a solution of (5,6-difluoro-1H-benzimidazol-2-yl)-(4-methylthiophen-3-yl)amine trifluoroacetic acid salt (15 mg, example 45) in glacial acetic acid (0.5 ml) in a ReactiVial, and the mixture was stirred at room temperature for 0.5 h. The acetic acid was then removed under reduced pressure and saturated potassium carbonate solution and ethyl acetate were added to the residue. The organic phase was removed and the aqueous phase was then extracted twice with ethyl acetate. The combined organic phases were dried using magnesium sulfate and the drying agent was then filtered off. The residue that remained after removal of the solvent under reduced pressure was purified by preparative chromatography. The product-containing fractions were combined and freed from acetonitrile, saturated sodium bicarbonate solution was added to the residue and the mixture was extracted three times with ethyl acetate. The organic phases were combined, dried (MgSO₄) and filtered. After removal of the ethyl acetate under reduced pressure, the residue was coevaporated with toluene and then dried under high vacuum. This gave 8.1 mg of the desired compound.

LCMS-Rt (D): 1.45 min

MS (ES⁺, M+H⁺): 343.96

Example 48

[(2-Chloro-4-methylthiophen-3-yl)-(4,5,6,7-tetrahydro-1H-benzimidazol-2-yl)]amine hydrochloride a) 1,4-Dioxaspiro[4.5]dec-6-ylamine

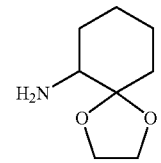

The amine required as precursor was prepared in accordance with GB1131191. 2-Chlorocyclohexanone was reacted with phthalimide to give 2-(2-oxocyclohexyl)isoindole-1,3-dione, which was ketalized with ethylene glycol in the presence of para-toluenesulfonic acid, giving 2-(1,4-dioxaspiro[4.5]dec-6-yl)isoindole-1,3-dione. Treatment with hydrazine hydrate to remove the phthalimideradical gave the desired 1,4-dioxaspiro[4.5]dec-6-ylamine.

b) 1-(1,4-Dioxaspiro[4.5]dec-6-yl)-3-(4-methylthiophen-3-yl)thiourea

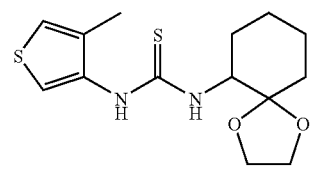

A solution of 3-isothiocyanato-4-methylthiophene (296.2 mg, see example 1a) in absolute tetrahydrofuran (10 ml) was added dropwise to a solution of 1,4-dioxaspiro[4.5]dec-6-ylamine (300 mg) in absolute tetrahydrofuran (10 ml), the mixture was stirred at room temperature for 2 hours and the solvent was then removed under reduced pressure. The residue was purified by preparative chromatography and the product-containing fractions were combined, freed from acetonitrile, made basic and extracted three times with ethyl acetate. The organic phases were combined, dried (MgSO4) and filtered. This gave 428 mg of the desired product.

LCMS-Rt (A): 3.57 min

MS (ES⁺, M+H⁺): 313.19 c) 1-(1,4-Dioxaspiro[4.5]dec-6-yl)-2-methyl-3-(4-methylthiophen-3-yl)isothiourea

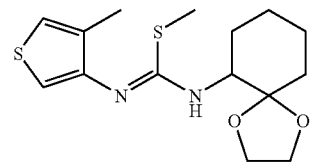

1-(1,4-Dioxaspiro[4.5]dec-6-yl)-3-(4-methylthiophen-3-yl)thiourea (393 mg) was dissolved in absolute tetrahydrofuran (8.5 ml), and a solution of methyl iodide (179 mg) in absolute tetrahydrofuran (0.5 ml) was added. The mixture was then stirred at 70° C. in sand bath for 2 days. Ethyl acetate was then added to the reaction mixture, and the mixture was washed twice with water. The organic phase was dried over magnesium sulfate and the solvent was removed after filtration. The residue was purified by preparative chromatography and the product-containing fractions were combined, freed from acetonitrile, made basic and extracted three times with ethyl acetate. The organic phases were combined, dried (MgSO$_4$) and filtered. This gave 59 mg of the desired product which was used directly for the next step.

LCMS-Rt (C): 1.05 min
MS (ES$^+$, M+H$^+$): 327.4 d) N-(1,4-Dioxaspiro[4.5]dec-6-yl)-N'-(4-methylthiophen-3-yl)guanidine

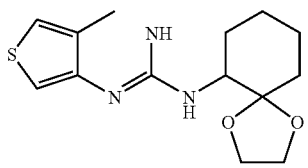

In a ReactiVial, a 7 M solution of ammonia in methanol (2 ml) was added to 1-(1,4-dioxaspiro[4.5]dec-6-yl)-2-methyl-3-(4-methylthiophen-3-yl)isothiourea (58.8 mg), and the mixture was heated in a sand bath at about 100° C. for 16 hours. Removal of the solvent gave a residue of 51 mg of an oily product which was directly reacted further.

LCMS-Rt (C): 1.00 min
MS (ES$^+$, M+H$^+$): 296.4 e) N-(2-Chloro-4-methylthiophen-3-yl)-N'-(1,4-dioxaspiro[4.5]dec-6-yl)guanidine

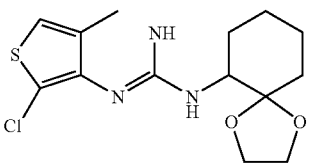

N-(1,4-Dioxaspiro[4.5]dec-6-yl)-N'-(4-methylthiophen-3-yl)guanidine (49 mg) was dissolved in glacial acetic acid (3 ml), and a solution of N-chlorosuccinimide (20.3 mg) in glacial acetic acid (5 ml) was added slowly. The mixture was stirred for a number of hours and then allowed to stand at room temperature over the weekend, after which the glacial acetic acid was removed under reduced pressure, the residue was taken up in water and the mixture was adjusted to pH 10 using 2N sodium hydroxide solution. The basic phase was extracted three times with ethyl acetate and the combined organic phases were dried over magnesium sulfate, filtered and concentrated. The residue was purified by preparative chromatography and the product-containing fractions were combined, freed from acetonitrile, made basic and extracted three times with ethyl acetate. The organic phases were combined, dried (MgSO$_4$) and filtered. Removal of the solvent under reduced pressure gave 24 mg of the desired product which was used directly for the next step.

LCMS-Rt (C): 1.09 min
MS (ES$^+$, M+H$^+$): 330.4 f) ((2-Chloro-4-methylthiophen-3-yl)-(4,5,6,7-tetrahydro-1H-benzoimidazol-2-yl))amine hydrochloride

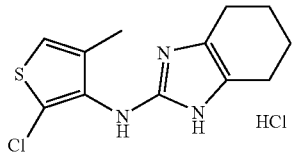

N-(2-Chloro-4-methylthiophen-3-yl)-N'-(1,4-dioxaspiro[4.5]dec-6-yl)guanidine (24 mg) was dissolved in 2N hydrochloric acid (1 ml) and stirred at room temperature for 30 min. Concentrated hydrochloric acid (1 ml) was then added, and the mixture was stirred for another two hours. The mixture was then diluted with a little water and freeze-dried. Toluene was added to the residue and then distilled off under reduced pressure. This step was repeated twice, giving 22 mg of the desired product as a solid.

LCMS-Rt (B): 0.95 min
MS (ES$^+$, M+H$^+$): 268.07

Example 49

2-Chloro-3N-(2-benzimidazolylamino)-4-methylthiophene Benzenesulfonate

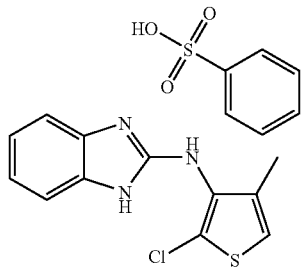

2-Chloro-3N-(2-benzimidazolylamino)-4-methylthiophene (250 mg) was dissolved in THF (5 ml), and benzenesulfonic acid (150 mg), dissolved in THF (5 ml), was added with stirring. After 3 h, the reaction mixture was left in the fridge overnight. The precipitate was filtered off with suction and dried at 75° C. under high vacuum, giving the desired product. Colorless crystals. M.p.: 235° C.

Example 50

2-Chloro-3N-(2-benzimidazolylamino)-4-methylthiophene Methanesulfonate

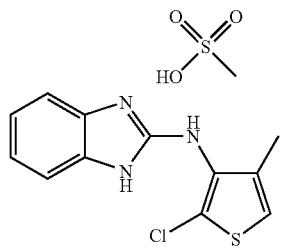

was obtained analogously to the procedure described in example 49 from 2-chloro-3N-(2-benzimidazolylamino)-4-methylthiophene using one equivalent of methanesulfonic acid. Colorless crystals. M.p.: 227° C.

Example 51

2-Chloro-3N-(2-benzimidazolylamino)-4-methylthiophene Benzoate

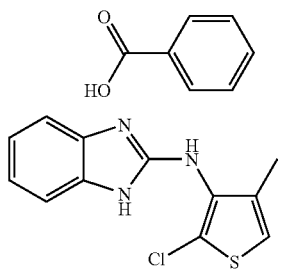

was obtained analogously to the procedure described in example 49 from 2-chloro-3N-(2-benzimidazolylamino)-4-methylthiophene using one equivalent of benzoic acid. For the precipitation, the reaction mixture was concentrated to half of its original volume, and ether (30 ml) was then added. Colorless crystals, m.p.: 198° C.

Example 52

2,4-Dichloro-3N-(2-benzimidazolylamino)thiophene hydrochloride

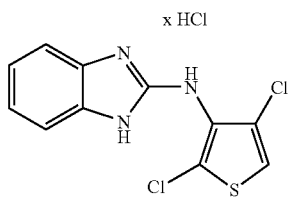

a) Methyl 3-acetylaminothiophene 2-carboxylate

With simultaneous heating in an oil bath, 567 ml of acetic anhydride are added dropwise to a mixture of 942 g of methyl 3-aminothiophene-2-carboxylate and 1000 ml of toluene, and the mixture is then boiled under reflux conditions for 1½ hours and subsequently cooled in an ice bath to about 0° C. The crystals are filtered off and washed twice with a little isopropanol and twice with diisopropyl ether. Methyl 3-acetylaminothiophene-2-carboxylate can be obtained from the filtrate by further concentration and crystallization. M.p. 93-95° C.

b) Methyl 3-acetylamino-4,5-dichlorothiophene-2-carboxylate

With magnetic stirring at a reaction temperature of 20-30° C., 17.9 g of sulfuryl chloride $SO_2Cl_2$ are added dropwise to a solution of 19.9 g of methyl 3-acetylaminothiophene-2-carboxylate in 100 ml of chloroform. The mixture is then stirred at 40° C. for another 2 hours and boiled under reflux conditions for another 15 minutes. The solvent is distilled off under reduced pressure, ethyl acetate is then added to the residue and the crystals are, after standing, filtered off. M.p. 136-138° C.

c) Methyl 3-acetylamino-4 chlorothiophene-2-carboxylate

A mixture of 25 g of methyl 3-acetylamino-4,5-dichlorothiophene-2-carboxylate, about 10 g of triethylamine, 300 ml of methanol and 1 g of palladium on carbon is, at room temperature and under atmospheric pressure, hydrogenated until the uptake of hydrogen has stopped. The catalyst is filtered off and the mixture is then concentrated by distillation under reduced pressure until crystallization begins, water is then added and the solid is filtered off. Colorless crystals from isopropanol. M.p. 142-147° C.

d) Methyl 3-amino-4-chlorothiophene-2-carboxylate

In a mixture of 50 ml of methanol and 50 ml of concentrated hydrochloric acid, 7 g of methyl 3-acetylamino-4-chlorothiophene-2-carboxylate are stirred at 60° C. for 4 hours, under reflux for 5 hours and at room temperature for another 3 days. Any precipitate that has formed is removed by filtration, and about ⅓ of the volume of the solvent is removed by distillation under reduced pressure. Following addition of about 100 ml of water, the mixture is stirred at room temperature for another 15 minutes and the colorless crystals are filtered off and dried in a stream of air. M.p.: 62-64° C.

e) 3-Amino-4-chlorothiophene 18.02 g of methyl 3-amino-4-chlorothiophene-2-carboxylate are added to a solution of 11.1 g of KOH and 160 ml of water and the mixture is then boiled under reflux for 3 hours and, after cooling, added dropwise to a solution, which is at 60° C., of 15 ml of concentrated hydrochloric acid and 30 ml of water. This results in a vigorous evolution of $CO_2$. After further stirring at 60° C. for about 40 minutes, the mixture is allowed to cool, a layer of 50-100 ml of methyl tert-butyl ether is added, the mixture is made alkaline using concentrated aqueous sodium hydroxide solution and the aqueous phase is extracted in a separating funnel. The aqueous phase is extracted two more times with methyl tert-butyl ether, and the combined organic extracts are washed once with water in a separating funnel. The organic phase is dried, the solvent is distilled off and the oily-amorphous residue is chromatographed on a silica gel column using a mixture of 1 part of ethyl acetate and 1 part of toluene.

f) 4-Chloro-3-thienyl isothiocyanate 1.46 g of thiocarbonyldiimidazole are added to a solution of 1.1 g of 3-amino-4-chlorothiophene in 20 ml of anhydrous THF, and the mixture is stirred at room temperature for one hour. The solid is distilled off under reduced pressure, the residue is dissolved in ethyl acetate, the organic phase is treated twice with water in a separating funnel and then dried, and the solvent is again distilled off under reduced pressure. This gives 4-chloro-3-thienyl isothiocyanate as a dark oil which is then reacted further without further purification steps.

g) N-(2-Aminophenyl)-N'-(4-chloro-3-thienyl)thiourea 0.86 g of 1,2-diaminobenzene (o-phenylenediamine) is added to a solution of 1.4 g of 4-chloro-3-thienyl isothiocyanate in 40 ml of anhydrous THF, the mixture is stirred at room temperature for about 20 hours and the solvent is distilled off under reduced pressure. The residue is treated with water and extracted with ethyl acetate, the solvent is distilled off again and the residue is purified using medium-pressure silica gel column chromatography using a 1:1 mixture of ethyl acetate and toluene. Brown-yellow solid.

h) 4-Chloro-3N-(2-benzimidazolylamino)thiophene

A solution of 0.169 g of sodium hydroxide in 5 ml of water, followed by a solution of 0.363 g of p-toluenesulfonyl chloride in 10 ml of THF, is added to a solution of 0.5 g of N-(2-aminophenyl)-N'-(4-chloro-3-thienyl)thiourea in 25 ml of anhydrous THF. The mixture is stirred at room temperature for 3 hours, the solvent is then distilled off under reduced pressure and the residue is treated with water and extracted with ethyl acetate. After removal of the solvent by distillation, the product is purified by medium-pressure silica gel chromatography using a mixture of 20 parts of ethyl acetate, 10 parts of n-heptane and 3 parts of glacial acetic acid as eluent.

For characterization, a small portion of the 4-chloro-3N-(2-benzimidazolylamino)-thiophene was, in ethyl acetate, using ethereal hydrogen chloride solution, converted into 4-chloro-3N-(2-benzimidazolylamino)thiophene hydrochloride and characterized. Colorless crystals. M.p.: 256-260° C.

i) 2,4-Dichloro-3N-(2-benzimidazolylamino)thiophene hydrochloride

A solution of 0.16 g of N-chlorosuccinimide in 5 ml of glacial acetic acid is added to a solution of 0.3 g of 4-chloro-3N-(2-benzimidazolylamino)thiophene in 10 ml of glacial acetic acid. The reaction mixture is stirred at 40° C. for 15 minutes and at room temperature for about 4 hours, the acetic acid is then distilled off under reduced pressure and the residue is treated with water. The mixture is made alkaline using aqueous sodium hydroxide solution and then extracted with ethyl acetate, the extract is washed with water, the organic phase is dried and the solvent is distilled off under reduced pressure. The residue is purified under medium-pressure conditions by column chromatography using a mixture of 20 parts of ethyl acetate, 10 parts of n-heptane and 3 parts of glacial acetic acid as eluent and then precipitated from ethyl acetate by addition of a solution of hydrogen chloride in diethyl ether. Colorless crystalline product. M.p. 264-268° C.

Example 53

2-Bromo-4-chloro-3N-(2-benzimidazolylamino)thiophene hydrochloride

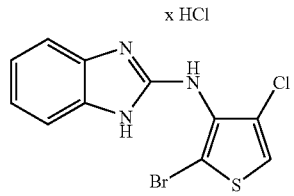

A solution of 0.356 g of N-bromosuccinimide in 6 ml of glacial acetic acid is added dropwise to a solution of 0.5 g of 4-chloro-3N-(2-benzimidazolylamino)thiophene in 15 ml of glacial acetic acid, and the mixture is stirred at room temperature for another 15 minutes. The solvent is distilled off and the residue is treated with water and made alkaline using aqueous sodium hydroxide solution. Following extraction with ethyl acetate, the organic phase is washed with water, dried and concentrated under reduced pressure. The residue is chromatographed on silica gel using medium-pressure conditions and a mixture of 20 parts of ethyl acetate, 10 parts of n-heptane and 3 parts of glacial acetic acid as eluent. Following distillative removal of the solvent, the residue is taken up in ethyl acetate and 2-bromo-4-chloro-3N-(2-benzimidazolylamino)thiophene hydrochloride is precipitated by addition of a solution of hydrogen chloride gas in diethyl ether. Colorless crystalline product. M.p.: 264-266° C.

Example 54

(2,4-Dichloro-thiophen-3-yl)-(5-fluoro-1H-benzoimidazol-2-yl)-amine-hydrochloride a) 1-(2-Amino-4-fluoro-phenyl)-3-(4-chloro-thiophen-3-yl)-thiourea

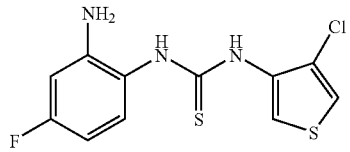

4-Fluoro-1,2-phenylendiamine (900 mg) was dissolved in THF (25 ml) and 4-chloro-3-thienylisothiocyanat (example 52c), dissolved in THF (15 ml), was added with stirring. The solution was stirred for about 3 h at room temperature and stood overnight. Then the reaction mixture was concentrated and the residue purified by preparative HPLC. The product containing fractions were combined, the acetonitrile was removed, the aqueous residue made basic and three times extracted with ethyl acetate. The organic layers were combined, dried (MgSO4) and filtered. After removal of the solvent the desired product (625 mg) was obtained.

LCMS-Rt (F): 1.28 min

MS (ES+, M+H+): 302.0 b) (4-Chloro-thiophen-3-yl)-(5-fluoro-1H-benzoimidazol-2-yl)-amine

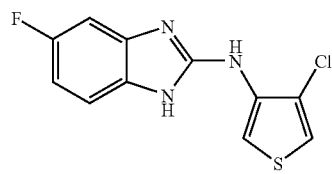

1-(2-Amino-4-fluoro-phenyl)-3-(4-chloro-thiophen-3-yl)-thiourea (625 mg) was dissolved in THF and a solution of NaOH (0.207 g) in water (9 ml) was added. Within 5 min a solution of p-toluenesulfonyl chloride (0.395 g) in THF (10 ml) was added dropwise. After stirring for one hour at room temperature water and ethyl acetate were added to the reaction mixture. The organic layer was separated and the aqueous phase was extracted three times with ethyl acetate. The combined organic layers were dried (MgSO4), treated with charcoal, filtered and the solvent evaporated to yield the desired product (135 mg).

LCMS-Rt (F): 0.90 min
MS (ES+, M+H+): 268.0 c) (2,4-Dichloro-thiophen-3-yl)-(5-fluoro-1H-benzoimidazol-2-yl)-amine hydrochloride

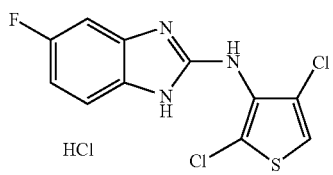

(4-Chloro-thiophen-3-yl)-(5-fluoro-1H-benzoimidazol-2-yl)-amine (85 mg) was dissolved in acetic acid (4 ml) and under vigorous stirring at room temperature a solution of N-chlorosuccinimide (42 mg) in acetic acid (4 ml) was added. After stirring for 45 min. at room temperature, stirring was continued for 5 h at 50° C. After the addition of further N-chlorosuccinimide (4 mg) stirring was continued for one hour at 50° C. Then the reaction mixture was treated with toluene (20 ml) and solvent mixture distilled off. The residue was dissolved in ethyl acetate and washed with saturated potassium carbonate solution. The organic layer was dried (MgSO4), filtered and concentrated. The residue was purified by preparative HPLC, the product containing fractions were combined, the acetonitrile was removed, the aqueous residue made basic and extracted three times with ethyl acetate. The organic layers were combined, dried (MgSO4) and filtered. After removal of the solvent water and 2 N HCl were added to the residue. After freeze drying the desired product (17 mg) was obtained.

LCMS-Rt (E): 2.65 min
MS (ES+, M+H+): 301.93

Example 55

(2-Bromo-4-chloro-thiophen-3-yl)-(5-fluoro-1H-benzoimidazol-2-yl)-amine hydrochloride

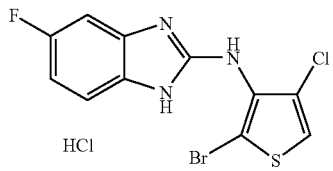

(4-Chloro-thiophen-3-yl)-(5-fluoro-1H-benzoimidazol-2-yl)-amine (50 mg, example 54b) was dissolved in acetic acid (4 ml) and at room temperature with vigorous stirring N-bromosuccinimide (33 mg) dissolved in acetic acid (4 ml) was slowly added. After stirring for 45 min at room temperature toluene (20 ml) was added and the solvent mixture distilled off. The residue was dissolved in ethyl acetate and washed with saturated potassium carbonate solution. The organic layer was dried (MgSO4), filtered and concentrated. The residue was purified by preparative HPLC, the product containing fractions were combined, the acetonitrile was removed, the aqueous residue set basic and three times extracted with ethyl acetate. The organic layers were combined, dried (MgSO4) and filtered. After removal of the solvent water and 2 N HCl were added to the residue. After freeze drying the desired product (27 mg) was obtained.

LCMS-Rt (E): 2.29 min
MS (ES+, M+H+): 347.87

Example 56

(2,4-Dichloro-thiophen-3-yl)-(5,6-difluoro-1H-benzoimidazol-2-yl)-amine-hydrochloride a) 1-(2-Amino-4,5-difluoro-phenyl)-3-(4-chloro-thiophen-3-yl)-thiourea

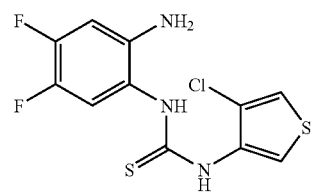

To 1,2-diamino-4,5-difluorobenzene (1.02 g) in THF abs. (15 ml) 4-chloro-3-thienylisothiocyanate (1.25 g, example 52c) dissolved in THF abs. (15 ml) was added. Following the analogous description in example 54a) the desired product was obtained (773 mg).

LCMS-Rt (F): 1.32 min
MS (ES+, M+H+): 320.0 b) (4-Chloro-thiophen-3-yl)-(5,6-difluoro-1H-benzoimidazol-2-yl)-amine

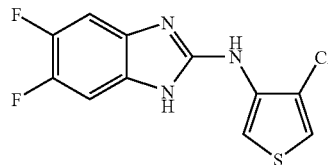

To 1-(2-amino-4,5-difluoro-phenyl)-3-(4-chloro-thiophen-3-yl)-thiourea (773 mg) in THF (20 ml) a solution of NaOH (240 mg) in water (9 ml) was added followed by a solution of p-toluenesulfonyl chloride (528 mg) in THF (10 ml). Following the analogous description in example 54b) the desired product (275 mg) was obtained.

LCMS-Rt (F): 0.95 min
MS (ES+, M+H+): 286 c) (2,4-Dichloro-thiophen-3-yl)-(5,6-difluoro-1H-benzoimidazol-2-yl)-amine-hydrochloride

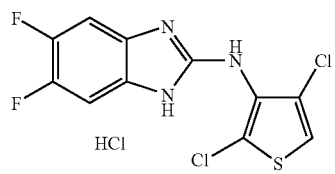

To (4-chloro-thiophen-3-yl)-(5,6-difluoro-1H-benzoimidazol-2-yl)-amine (125 mg) in acetic acid (8 ml) a solution of N-chlorosuccinimide (59 mg) in acetic acid (2 ml) was added. Following the analogous description in example 54c) the desired product (58 mg) was obtained.

LCMS-Rt (E): 2.97 min
MS (ES+, M+H+): 319.88

Example 57

(2-Bromo-4-chloro-thiophen-3-yl)-(5,6-difluoro-1H-benzoimidazol-2-yl)-amine-hydrochloride

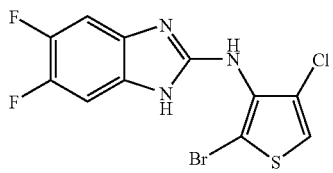

To (4-chloro-thiophen-3-yl)-(5,6-difluoro-1H-benzoimidazol-2-yl)-amine (125 mg, example 55b) in acetic acid (8 ml) N-bromosuccinimide (78 mg) dissolved in acetic acid was added under vigorous stirring at room temperature. Following the analogous description in example 55) the desired product (77 mg) was obtained.

LCMS-Rt (E): 2.39 min
MS (ES+, M+H+): 365.86

Example 58

4-Chloro-3N-(4-methyl-2-benzimidazolyl-amino)thiophene Hydrochloride

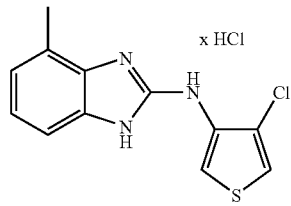

a) N-(2-Amino-3-methylphenyl)-N'-(4-chloro-3-thienyl)thiourea was obtained as described in example 52 g) by using 4-chloro-3-thienylisothiocyanate and 1,2-diamino-3-methyl-benzene and chromatographical purification (silica gel, ethyl acetate/n-heptane/glacial acetic acid=20:10:3). Brownish-yellowish solid, Mp.: 193-196° C.

b) e) 4-Chloro-3N-(4-methyl-2-benzimidazolylamino)thiophene was obtained as described in example 52h) by using N-(2-Amino-3-methylphenyl)-N'-(4-chloro-3-thienyl)thiourea and chromatographical purification (silica gel, dichloromethane/methanol=10:1). The amorphous, foamy material was dissolved in ethyl acetate and treated with a solution of gaseous HCl in diethyl ether forming 4-chloro-3N-(4-methyl-2-benzimidazolylamino)thiophen hydrochloride. Crystalline material, m.p. 325-327° C.

Example 59

2,4-Dichlor-3N-(4-methyl-2-benzimidazolyl-amino)thiophen Hydrochloride

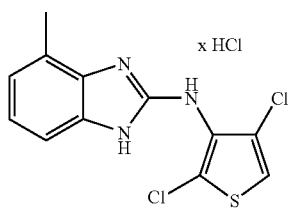

was obtained as described in example 52i) by reaction of 4-chloro-3N-(4-methyl-2-benzimidazolylamino)thiophene and N-chlorosuccinimide in pure acetic acid and by analogeous purification. Crystalline material, m.p. 296-298° C.

Example 60 trans-(3aS,7aS)-4-Chloro-3N-(3a,4,5,6,7,7a-hexahydro-1H-2-benzimidazolyl)-3-thienylamine Hydrochloride

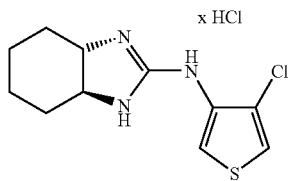

a) trans-S,S-3N-(2-Amino-cyclohexyl)-N'-(4-chloro-3-thienyl)-thiourea was obtained as described in example 1 b) by reaction of 4-chloro-3-thienyl-isothiocyanate and trans-S,S-1,2-diaminocyclohexane. Chromatographical purification (silica gel, ethylacetate/dichloromethane/n-heptane/methanol/aqueous ammonia [35%]=10:5:5:5:1) results in a dark amorpheous material which was used for further syntheses without further purification.

b) trans-(3aS,7aS)-4-Chloro-3N-(3a,4,5,6,7,7a-hexahydro-1H-2-benzimidazolyl)-3-thienylamine was obtained as described in example 52h) by using trans-S,S-3N-(2-amino-cyclohexyl)-N'-(4-chloro-3-thienyl)-thiourea and p-Toluolsulfonylchloride. Chromatographical purification (silica gel, dichloromethane/methanol=10:1) results in an amorpheous material which can be transformed to the corresponding trans-S,S-4-chloro-3N-(3a,4,5,6,7,7a-hexahydro-1H-2-benzimidazolyl)-3-thienylamine hydrochloride by dissolving in ethylacetate and treatment with a solution of gaseous HCl in diethylether. Crystalline material, m.p. 196-200° C.

Example 61 trans-(3aR,7aR)-4-Chloro-3N-(3a,4,5,6,7,7a-hexahydro-1H-2-benzimidazolyl)-3-thienylamine Hydrochloride

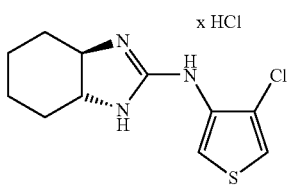

a) trans-(1R,2R)-3N-(2-Amino-cyclohexyl)-N'-(4-chloro-3-thienyl)-thiourea was obtained as described in example 1 b) by reaction of 4-chloro-3-thienyl-isothiocyanate and trans-(1R,2R)-(−)-1,2-diaminocyclohexane. Chromatographical purification (silica gel, ethylacetate/dichloromethane/n-heptane/methanol/aqueous ammonia [35%]=10:5:5:5:1) results in a dark amorpheous material which was used for further syntheses without further purification.

b) trans-(3aR,7aR)-4-Chloro-3N-(3a,4,5,6,7,7a-hexahydro-1H-2-benzimidazolyl)-3-thienylamine was obtained as described in example 52h) by using of trans-R,R-3N-(2-amino-cyclohexyl)-N'-(4-chloro-3-thienyl)-thiourea and p-toluolsulfonylchloride. Chromatographical purification (silica gel, ethylacetate/dichloromethane/n-heptane/methanol/aqueous ammonia [35%]=10:5:5:5:1) results in an amorpheous material which can be transformed to the corresponding trans-R,R-4-chloro-3N-(3a,4,5,6,7,7a-hexahydro-1H-2-benzimidazolyl)-3-thienylamine hydrochloride by dissolving the material in ethylacetate and treatment with a solution of gaseous HCl in diethylether. Crystalline material, m.p. 240-244° C.

Example 62 cis-4-Chloro-3N-(3a,4,5,6,7,7a-hexahydro-1H-2-benzimidazolyl)-3-thienylamine Hydrochloride

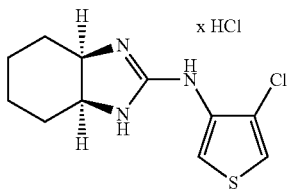

a) cis-3N-(2-Amino-cyclohexyl)-N'-(4-chloro-3-thienyl)-thiourea was obtained as described in example 1 b) by reaction of 4-chloro-3-thienyl-isothiocyanate and cis-1,2-diaminocyclohexane. Chromatographical purification (silica gel, ethylacetate/dichloromethane/n-heptane/methanol/aqueous ammonia [35%]=10:5:5:5:1) results in a dark amorpheous material which was used for further syntheses without further purification.

b) cis-4-Chloro-3N-(3a,4,5,6,7,7a-hexahydro-1H-2-benzimidazolyl)-3-thienylamine was obtained as described in example 52h) by using 3N-(cis-2-Amino-cyclohexyl)-N'-(4-chlor-3-thienyl)-thioharnstoff and p-Toluenesulfonyl chloride. Chromatographical purification (silica gel, ethylacetate/dichloromethane/n-heptane/methanol/aqueous ammonia [35%]=10:5:5:5:1) results in an amorpheous brownish material which can be transformed to the corresponding 4-chloro-3N-(cis-3a,4,5,6,7,7a-hexahydro-1H-2-benzimidazolyl)-3-thienylamine hydrochloride by dissolving in ethylacetate and treatment with a solution of gaseous HCl in diethylether. Crystalline material, m.p. 228-231° C.

Example 63 trans-R,R-2,4-Dichloro-3N-(3a,4,5,6,7,7a-hexahydro-1H-2-benzimidazolyl)-3-thienylamine Hydrochloride

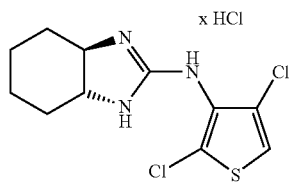

was obtained as described in example 52i) by reaction of trans-R,R-4-chloro-3N-(3a,4,5,6,7,7a-hexahydro-1H-2-benzimidazolyl)-3-thienylamine and N-chlorosuccinimide in pure acetic acid and by analogeous purification. Crystalline material, m.p. 296-298° C.

Example 64 cis-2,4-Dichloro-3N-(3a,4,5,6,7,7a-hexahydro-1H-2-benzimidazolyl)-3-thienylamine Hydrochloride

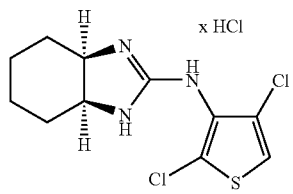

was obtained as described in example 52i) by reaction of cis-4-chloro-3N-(3a,4,5,6,7,7a-hexahydro-1H-2-benzimidazolyl)-3-thienylamine and N-chlorosuccinimide in pure acetic acid and by analogeous purification. Crystalline material, m.p. 270-274° C.

Example 65

4-Chloro-3N-(4-chloro-2-benzimidazolylamino)thiophene Hydrochloride

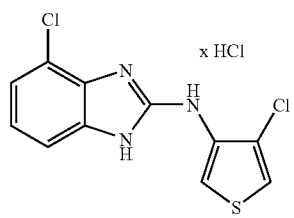

a) 1-N-(2-Amino-3-chlorophenyl)-3-N-(4-chloro-3-thienyl)thiourea was obtained as described in example 1 b) by reaction of 4-chloro-3-thienyl-isothiocyanate and 3-chloro-1,2-diaminobenzene. The compound crystallizes after stirring in diisopropylether. Solid crystalline material with 2 melting points: $1^{st}$ m.p. 152-155° C.; $2^{nd}$ m.p. (after recrystallization of molten material)>310° C.

b) 4-Chloro-3N-(4-chloro-2-benzimidazolylamino)thiophene was obtained as described in example 52h) using 1-N-(2-amino-3-chlorophenyl)-3-N-(4-chloro-3-thienyl)thiourea and p-toluenesulfonyl chloride. After chromatographic purification (silica gel, toluene/ethylacetate=3:1) the product was transformed to 4-chloro-3N-(4-chloro-2-benzimidazolylamino)thiophene hydrochloride by dissolving in ethylacetate and treatment with a solution of gaseous HCl in diethylether. Crystalline material, m.p. 276-280° C.

Example 66

2,4-Dichloro-3N-(4-chloro-2-benzimidazolyl-amino)thiophene Hydrochloride

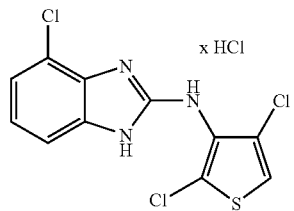

was obtained as described in example 52i) by reaction of 4-chloro-3N-(4-methyl-2-benzimidazolylamino)thiophene and N-chlorosuccinimide in pure acetic acid and by analogeous purification. Crystalline material, m.p. 294-297° C.

Analogously to the compounds listed in the working examples, it is possible to prepare the following thiophene derivatives:

2-bromo-4-chloro-3N-(4-methyl-2-benzimidazolyl-amino)thiophen hydrochloride, 2-bromo-4-chloro-3N-(4-chlor-2-benzimidazolyl-amino)thiophen hydrochloride, trans-R,R-2-bromo-4-chloro-3N-(3a,4,5,6,7,7a-hexahydro-1H-2-benzimidazolyl)-3-thienylamin hydrochloride, trans-(3aS,7aS)-2-bromo-4-chloro-3N-(3a,4,5,6,7,7a-hexahydro-1H-2-benzimidazolyl)-3-thienylamin hydrochloride, 2,4-dibromo-3N-(2-benzimidazolyl)-3-thienylamine hydrochloride, 2,4-dimethyl-3N-(2-benzimidazolyl)-3-thienylamine hydrochloride, 2,4-dimethyl-3N-(4-methyl-2-benzimidazolyl)-3-thienylamine hydrochloride, 2,4-dimethyl-3N-(5-fluoro-2-benzimidazolyl)-3-thienylamine hydrochloride, 2-chloro-3N-(4-butoxy-2-benzimidazolyl)-4-methyl-3-thienylamine hydrochloride, 2-chloro-3N-(4-trifluoromethyl-2-benzimidazolyl)-4-methyl-3-thienylamine hydrochloride, 2-chloro-3N-(4-methylsulfonyl-2-benzimidazolyl)-4-methyl-3-thienylamine hydrochloride.

Pharmacological Data:

Test Description:

In this test, the recovery of the intracellular pH (pHi) after an acidification, which starts when the NHE is capable of functioning, even under bicarbonate-free conditions, was determined. For this purpose, the pHi was determined using the pH-sensitive fluorescent dye BCECF (Calbiochem, the precursor BCECF-AM is employed). The cells were initially loaded with BCECF. The BCECF fluorescence was determined in a "ratio fluorescence spectrometer" (Photon Technology International, South Brunswick, N.J., USA) with excitation wavelengths of 505 and 440 nm and an emission wavelength of 535 nm, and was converted into the pHi using calibration plots. The cells were incubated in $NH_4Cl$ buffer (pH 7.4) ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 is established with 1 M NaOH) even during the BCECF loading. The intracellular acidification was induced by addition of 975 µl of an $NH_4Cl$-free buffer (see below) to 25 µl aliquots of the cells incubated in $NH_4Cl$ buffer. The subsequent rate of pH recovery was recorded in the case of NHE1 for two minutes, in the case of NHE2 for five minutes and in the case of NHE3 for three minutes. To calculate the inhibitory power of the tested substances, the cells were initially investigated in buffers in which complete or absolutely no pH recovery took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 is established with 1 M NaOH). To determine the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 is established with 1 M KOH). The substances to be tested were made up in the $Na^+$-containing buffer. Recovery of the intracellular pH at each tested concentration of a substance was expressed as a percentage of the maximum recovery. Using the Sigma-Plot program, the IC50 value of the substance in question was calculated for the individual NHE subtypes using the percentages for pH recovery.

Results:

| Example | IC$_{50}$ [μM] |
|---|---|
| 16 trans-R,R-2-chloro-3N-(3a,4,5,6,7,7a-hexahydro-1H-2-benzimidazolyl)-4-methyl-3-thienylamine hydrochloride | 0.27 (rNHE3) |
| 12 2-chloro-3N-(2-benzimidazolyl)-4-methyl-3-thienylamine hydrochloride | 0.12 (rNHE3) |
| 54: 2-bromo-4-chloro-3N-(2-benzimidazolylamino)thiophen hydrochloride | 0.22 (hNHE3) |
| 53: 2,4-dichloro-3N-(2-benzimidazolylamino)thiophen hydrochloride | 0.14 (hNHE3) |
| 56: 2,4-dichloro-3N-(4-methyl-2-benzimidazolyl-amino)thiophen hydrochloride | 0.22 (hNHE3) |
| 60: trans-R,R-2,4-dichloro-3N-(3a,4,5,6,7,7a-hexahydro-1H-2-benzimidazolyl)-3-thienylamin hydrochloride | 0.19 (hNHE3) |
| 63: 2,4-dichloro-3N-(4-chloro-2-benzimidazolyl-amino)thiophen hydrochloride | 0.54 (hNHE3) |
| 38: 2-chloro-3N-(4-hydroxy-2-benzimidazolyl-amino)-4-methylthiophen hydrochlorid | 0.84 (hNHE3) |
| 18: 2-bromo-3N-(2-benzimidazolyl)-4-methyl-3-thienylamin hydrochloride | 0.12 (hNHE3) |
| 19: trans-R,R-2-bromo-3N-(3a,4,5,6,7,7a-Hexahydro-1H-2-benzimidazolyl)-4-methyl-3-thienylamin hydrochloride | 0.56 (hNHE3) |
| 2: 2-chloro-3N-(5-fluoro-2-benzimidazolyl)-4-methyl-3-thienylamin hydrochloride | 0.62 (hNHE3) |
| 44: (1H-benzimidazol-2-yl)-(2-chloro-4-methyl-thiophen-3-yl)-methyl-amin | 1.59 (hNHE3) |

While there have been described and pointed out fundamental novel features of the invention as applied to a preferred embodiment thereof, it will be understood that various omissions and substitutions and changes, in the form and details of the packages and methods illustrated, may be made by those skilled in the art without departing from the invention. For example, it is expressly intended that all combinations of those elements and/or method steps which perform substantially the same function in substantially the same way to achieve the same results are within the scope of the invention.

The invention is not limited by the embodiments described above which are presented as examples only but can be modified in various ways within the scope of protection defined by the appended patent claims.

We claim:

1. A method for treating acute kidney failure or chronic kidney failure, in a patient in need thereof, comprising administering to the patient a pharmaceutical composition comprising a compound of formula I or a pharmaceutically acceptable salt thereof

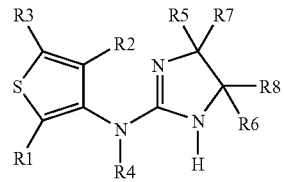

I wherein:
R1 and R2 are, independently, H, F, Cl, Br, I, CN, NO$_2$, —(X)$_n$—C$_q$H$_{2q}$—Z, cycloalkyl having 3, 4, 5 or 6 carbon atoms, alkenyl having 2, 3 or 4 carbon atoms, alkenylalkyl having 3 or 4 carbon atoms, ethynyl, or alkylalkynyl having 3 or 4 carbon atoms, wherein
n is zero or 1;
X is oxygen, NH, N—CH$_3$, or S(O)$_k$, wherein k is zero, 1 or 2;
q is zero, 1, 2, 3, 4, 5 or 6; and
Z is hydrogen or C$_m$F$_{2m+1}$, wherein m is zero, 1, 2, 3 or 4;
R3 is hydrogen, methyl, F, Cl, Br, I, CN, S(O)$_k$—CH$_3$, —NO$_2$, or —O—CH$_3$, wherein
k is zero, 1 or 2;
R4 is hydrogen, cycloalkyl having 3, 4, 5, or 6 carbon atoms, alkenyl having 2, 3 or 4 carbon atoms, alkenylalkyl having 3 or 4 carbon atoms, ethynyl, alkylalkynyl having 3 or 4 carbon atoms, or —C$_r$H$_{2r}$—Y, wherein
r is zero, 1, 2, 3 or 4; and
Y is hydrogen or trifluoromethyl;
R5 and R6 are hydrogen or are together a bond; and
R7 and R8 are, independently, (C$_3$-C$_5$)-alkyl, (C$_2$-C$_5$)-alkenyl, (C$_2$-C$_5$)-alkynyl, (C$_3$-C$_6$)-cycloalkyl or (C$_4$-C$_6$)-cycloalkenyl; or
R7 and R8 taken together with the two carbon atoms to which R7 and R8 are attached, form a (C$_5$-C$_{10}$) cycloalkyl ring which may be unsubstituted or substituted with one or more fluorine atoms; or
R7 and R8 taken together with the two carbon atoms to which R7 and R8 are attached, form a ring of the following formula

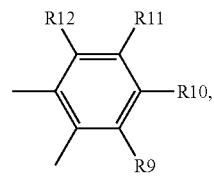

wherein
R10 and R11 are, independently, hydrogen, fluorine, chlorine, bromine, methyl, CN, OH, —O—CH$_3$, NO$_2$, NH$_2$ or —CF$_3$;
R9 and R12 are hydrogen or F; or
R9 is hydrogen and R12 is F, Cl, Br, I, CN, NO$_2$, COOH, CO—NR13R14, SO$_2$—NR13R14, alkenyl having 2, 3 or 4 carbon atoms, alkenylalkyl having 3 or 4 carbon atoms, ethynyl, alkylalkynyl having 3 or 4 carbon atoms, or —(XI)$_n$—C$_q$H$_{2q}$—Z; or
R12 is hydrogen and R9 is F, Cl, Br, I, CN, NO$_2$, COOH, CO—NR13R14, SO$_2$—NR13R14, alkenyl having 2, 3 or 4 carbon atoms, alkenylalkyl having 3 or 4 carbon atoms, ethynyl, alkylalkynyl having 3 or 4 carbon atoms, or —(XI)$_n$—C$_q$H$_{2q}$—Z; wherein:
R13 is hydrogen or alkyl having 1, 2, 3 or 4 carbon atoms and R14 is hydrogen or alkyl having 1, 2, 3, or 4 carbon atoms; or
R13 and R14 together with the nitrogen to which they are attached form a saturated 5-, 6- or 7-membered ring;
n is zero or 1;
XI is oxygen, NH, N—CH$_3$, or S(O)$_k$;
k is zero, 1 or 2;
q is zero, 1, 2, 3, 4, 5 or 6; and
Z is hydrogen or C$_m$F$_{2m+1}$, wherein m is zero, 1, 2, 3 or 4.

2. The method according to claim 1, wherein the pharmaceutical composition further comprises one or more other drugs or active compounds.

3. The method according to claim 1, wherein for the compound of formula I according to claim 1,
R1 and R2 are, independently, selected from the group consisting of H, F, Cl, Br, CH$_3$, CF$_3$, and SO$_2$CH$_3$, provided that R1 and R2 are not both hydrogen;
R3 is hydrogen, F or Cl;
R4 is hydrogen, alkyl having 1, 2, 3 or 4 carbon atoms, or cyclopropyl; and
R7 and R8 taken together with the two carbon atoms to which R7 and R8 are attached, form a (C$_5$-C$_{10}$) cycloalkyl ring which may be unsubstituted or substituted with one or more fluorine atoms; or
R7 and R8 taken together with the two carbon atoms to which R7 and R8 are attached, form a ring of the following formula

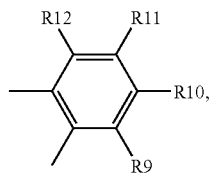

wherein,
R10 and R11 are, independently, hydrogen, OH, fluorine or chlorine;
R9 and R12 are both hydrogen, or
R9 is hydrogen and R12 is F, Cl, Br, CN, COOH, CO—NR13R14, SO$_2$—NR13R14 or —(XI)$_n$—C$_q$H$_{2q}$—Z, or
R12 is hydrogen and R9 is F, Cl, Br, CN, COOH, CO—NR13R14, SO$_2$—NR13R14 or —(XI)$_n$—C$_q$H$_{2q}$—Z, wherein
R13 and R14 are, independently, hydrogen or methyl;
n is zero or 1;
XI is oxygen, NH, N—CH$_3$ or S(O)$_k$;
k is zero, 1 or 2;
q is zero, 1, 2, 3 or 4; and
Z is hydrogen or CF$_3$.

4. The method according to claim 1, wherein for the compound of formula I according to claim 1,
R1 and R2 are, independently, F, Cl, Br, CH$_3$ or CF$_3$;
R3 is hydrogen;
R4 is hydrogen, methyl or ethyl; and
R7 and R8 taken together with the two carbon atoms to which R7 and R8 are attached, form a (C$_5$-C$_{10}$) cycloalkyl ring which may be unsubstituted or substituted with one or more fluorine atoms; or
R7 and R8 taken together with the two carbon atoms to which R7 and R8 are attached, form a ring of the following formula:

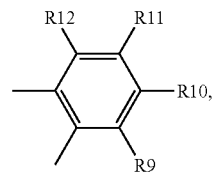

wherein,
R10 and R11 are, independently, hydrogen, OH or fluorine;
R9 and R12 are both hydrogen, or
R9 is hydrogen and R12 is F, Cl, Br or —(XI)$_n$—C$_q$H$_{2q}$—Z, or
R12 is hydrogen and R9 is F, Cl, Br or —(XI)$_n$—C$_q$H$_{2q}$—Z, wherein:
n is zero or 1;
XI is oxygen, NH, N—CH$_3$ or S(O)$_k$;
k is zero, 1 or 2;
q is zero or 1; and
Z is hydrogen or CF$_3$.

5. The method according to claim 1, wherein the compound of formula I according to claim 1 is
trans-R,R-2-chlorine-3N-(3a,4,5,6,7,7a-hexahydro-1H-2-benzimidazolyl)-4-methyl-3-thienylamine,
trans-R,R-2-bromo-3N-(3a,4,5,6,7,7a-hexahydro-1H-2-benzimidazolyl)-4-methyl-3-thienylamine,
2-chloro-3N-(2-benzimidazolyl)-4-methyl-3-thienylamine,
2-bromo-3N-(2-benzimidazolyl)-4-methyl-3-thienylamine,
2-chloro-3N-(4-methyl-2-benzimidazolyl)-4-methyl-3-thienylamine,
2-chloro-3N-(5-fluoro-2-benzimidazolyl)-4-methyl-3-thienylamine,
2-chloro-3N-(4-chloro-2-benzimidazolylamino)-4-methylthiophene,
2-bromo-3N-(4-chloro-2-benzimidazolylamino)-4-methylthiophene,
2-bromo-3N-(4-fluoro-2-benzimidazolylamino)-4-methylthiophene,
2-chloro-3N-(4-fluoro-2-benzimidazolylamino)-4-methylthiophene,
2-chloro-3N-(4-hydroxy-2-benzimidazolylamino)-4-methylthiophene,
(1H-benzimidazol-2-yl)-(2-chloro-4-methylthiophen-3-yl)-methylamine,
(2-bromo-4-methylthiophen-3-yl)-(5-fluoro-1H-benzimidazol-2-yl)-amine,
2,4-dichloro-3N-(2-benzimidazolylamino)thiophene,
2-bromo-4-chloro-3N-(2-benzimidazolylamino)thiophene,
2,4-dichloro-3N-(4-methyl-2-benzimidazolyl-amino)thiophene,
trans-R,R-2,4-dichloro-3N-(3a,4,5,6,7,7a-hexahydro-1H-2-benzimidazolyl)-3-thienylamine,
2,4-dichloro-3N-(4-chloro-2-benzimidazolyl-amino)thiophene, or
2-chloro-3N-(2-benzimidazolylamino)-4-methylthiophene.

* * * * *